US010336759B2

(12) United States Patent
Qiao et al.

(10) Patent No.: US 10,336,759 B2
(45) Date of Patent: Jul. 2, 2019

(54) SALTS AND PROCESSES OF PREPARING A PI3K INHIBITOR

(71) Applicant: Incyte Corporation, Wilmington, DE (US)

(72) Inventors: Lei Qiao, Downingtown, PA (US); Lingkai Weng, Phoenixville, PA (US); David Meloni, Bear, DE (US); Zhongjiang Jia, Kennett Square, PA (US); Jianji Wang, New Castle, DE (US); Jiacheng Zhou, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/054,474

(22) Filed: Feb. 26, 2016

(65) Prior Publication Data

US 2016/0257689 A1    Sep. 8, 2016

Related U.S. Application Data

(60) Provisional application No. 62/121,697, filed on Feb. 27, 2015.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC combination set(s) only.
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmerman |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,598,257 B2 | 10/2009 | Rodgers et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 9,096,600 B2 | 8/2015 | Li et al. |
| 9,199,982 B2 | 12/2015 | Li et al. |
| 9,249,087 B2 | 2/2016 | Kozikowski et al. |
| 9,309,251 B2 | 4/2016 | Combs et al. |
| 9,434,746 B2 | 9/2016 | Li et al. |
| 9,527,848 B2 | 12/2016 | Li et al. |
| 9,707,233 B2 | 7/2017 | Li et al. |
| 9,730,939 B2 | 8/2017 | Li et al. |
| 9,815,839 B2 | 11/2017 | Li et al. |
| 10,077,277 B2 | 9/2018 | Li et al. |
| 10,092,570 B2 | 10/2018 | Li et al. |
| 10,125,150 B2 | 11/2018 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

Berge et al, Review Article, Pharmaceutical Salts, vol. 66, No. 1, Jan. 1997, pp. 1-19.*

(Continued)

*Primary Examiner* — Jean P Cornet
(74) *Attorney, Agent, or Firm* — Fish & Richardson P.C.

(57) ABSTRACT

The present application provides processes for preparing (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one, which is useful as an inhibitor phosphoinositide 3-kinase-delta (PI3Kδ), as well as a salt form and intermediates related thereto.

8 Claims, 3 Drawing Sheets

(56) References Cited

U.S. PATENT DOCUMENTS

| | | |
|---|---|---|
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikan et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0166164 A1 | 7/2011 | Brewster |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1* | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2016/0022685 A1 | 1/2016 | Li et al. |
| 2016/0024117 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |
| 2016/0362426 A1 | 12/2016 | Zhou et al. |
| 2017/0050987 A1 | 2/2017 | Li et al. |
| 2017/0158696 A1 | 6/2017 | Li et al. |
| 2018/0258105 A1 | 9/2018 | Li et al. |
| 2018/0362546 A1 | 12/2018 | Li et al. |
| 2019/0002470 A1 | 1/2019 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 200080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 1993/16076 | 8/1993 |
| WO | WO 1993/22291 | 11/1993 |
| WO | WO 1993/25524 | 12/1993 |
| WO | WO 1999/43651 | 9/1999 |
| WO | WO 1999/43672 | 9/1999 |
| WO | WO 2000/09495 | 2/2000 |
| WO | WO 2000/044750 | 8/2000 |
| WO | WO 2000/053595 | 9/2000 |
| WO | WO 2001/014402 | 3/2001 |
| WO | WO 2001/064639 | 9/2001 |
| WO | WO 2001/064655 | 9/2001 |
| WO | WO 2001/072709 | 10/2001 |
| WO | WO 2002/000196 | 1/2002 |
| WO | WO 2002/006477 | 1/2002 |
| WO | WO 2002/024685 | 3/2002 |
| WO | WO 2002/064599 | 8/2002 |
| WO | WO 2002/066478 | 8/2002 |
| WO | WO 2002/078701 | 10/2002 |
| WO | WO 2003/020721 | 3/2003 |
| WO | WO 2003/024967 | 3/2003 |
| WO | WO 2003/029209 | 4/2003 |
| WO | WO 2003/037103 | 5/2003 |
| WO | WO 2003/044014 | 5/2003 |
| WO | WO 2003/049678 | 6/2003 |
| WO | WO 2003/050064 | 6/2003 |
| WO | WO 2003/068750 | 8/2003 |
| WO | WO 2003/074497 | 9/2003 |
| WO | WO 2003/099771 | 12/2003 |
| WO | WO 2004/005281 | 1/2004 |

(56) References Cited

FOREIGN PATENT DOCUMENTS

| | | |
|---|---|---|
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013/151930 | 10/2013 |
| WO | WO 2015/191677 | 12/2015 |
| WO | WO 2016/183063 | 6/2016 |
| WO | WO 2016/183060 | 11/2016 |
| WO | WO 2016/183062 | 11/2016 |

OTHER PUBLICATIONS

"A to Z List of Cancers," National Cancer Institute (http://www.cancer.gov/) (Downloaded May 29, 2014), 22 pages.

"Angiogenesis" Merriam-Webster.com. Merriam-Webster, n.d. Web Jun. 16, 2014, www.merriam-webster.com/dictionary/angiogenesis, 3 pages.

"Arthritis: MedlinePlus Medical Encyclopedica," 2014, p. 1-5, accessed online Oct. 7, 2014; http://www.nlm.nih.gove/medlineplus/ency/article/001243.htm.

"Autoimmune disorders: MedlinePlus Medical Encyclopedia," 2013, p. 1-4, accessed online Oct. 7, 2014; http://www.nlm.nih.gov/medlineplus/ency/article/000816.htm.

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential role for the p110δ phosphoinositide 3-kinase in the allergic response," Nature. 2004, 431(7011):1007-11.

Allen, et al., "Synthesis of C-6 substituted pyrazolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl. Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Bather, et al., "PI3Kγ inhibition blocks glomerulonephritis and extends lifespan in a mouse model of systemic lupus," Nat Med. 2005, 11(9):933-5.

Barragan et al., "Protein Kinases in the Regulation of Apoptosis in B-cell Chronic Lymphocytic Leukemia," *Leukemia and Lymphoma*, 2003, 44(11):1865-1870.

(56) References Cited

OTHER PUBLICATIONS

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Bendell, J.C., "Phase I, dose-escalation study of BKM120, an oral pan-Class I PI3K inhibitor, in patients with advanced solid tumors," Journal of Clincial Oncology (2011): JCO-2011.

Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Berge et al., "Pharmaceutical Salts," J Pharma Sci, 1977, 66(1):1-19.

Bergman, et al., "Synthesis of indolocarbazole quinones; potent aryl hydrocarbon receptor ligands," *Tetrahedron* (2002), 58(7), 1443-1452.

Bhatia and Rose, "Autoimmunity and autoimmune disease," Principles of Med Biol., 1996, 6:239-263, 244.

Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.

Billottet, et al., "A selective inhibitor of the p110δ isoform of PI 3-kinase inhibits AML cell proliferation and survival and increases the cytotoic effects of VP16," Oncogene. 2006, 25(50):6648-59.

Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.

Blom et al., Preparative LC-MS Purification: Improved Compound Specific Method Optimization, J. Combi. Chem. 2004, 6(6), 874-883.

Blom et al., "Two-Pump at Column Dilution Configuration for Preparative LC-MS," 2002, 4: 295.

Blom et al., "Optimizing Preparative LC-MS Configurations and Methods for Parallel Synthesis Purification," 2003, 5: 670.

Boger, et al., "First and Second Generation Total Synthesis of the Teicoplanin Aglycon," JACS, 123(9), 1862-1871, 2001.

Brachmann et al., "PI3K and mTOR inhibitors—a new generation of targeted anticancer agents," Current Opinion Cell Biol., 2009, 21:194-198.

Bringmann, et al., "Novel concepts in directed biaryl synthesis. Part 65. Synthesis and structure of a novel twofold lactone-bridged tennaphthyl," *Tetrahedron Letters* (1998), 39(12), 1545-1548 CODEN: TELEAY; ISSN: 0040-4039.

Brock et al., "Roles of Gβγ in membrane recruitment and activation of p110γ/p101 phosphoinositide 3-kinaseγ," J Cell Biol., 2003, 160(1):89-99.

Brown, et al., "Small molecule inhibitors of IgE synthesis," *Bioorganic & Medicinal Chemistry Letters* (2006), 16(17), 4697-4699.

Cacoub et al., "Anti-CD20 monoclonal antibody (rituximab) treatment for cryoglobulinemic vasculitis: where do we stand?," Ann Rheum Dis, Mar. 2008, 67: 283-287.

Camps, et al., "Blockade of PI3Kγ suppresses joing inflammation and damage in mouse models of rheumatoid arthritis," Nat Med. 2005, 11(9):936-43.

Cannon, Burger's Medicinal Chemistry and Drug Discovery, Fifth Edition, vol. 1 Principles and Practice, Wiley-Interscience 1995, Ch. 19, pp. 783-803, 784.

Cantley, "The Phosphoinositide 3-Kinase Pathway," Science, (2002) 296 (5573):1655-7.

Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.

Chai, et al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.

Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.

Chen, X., "Targeting oxidative stress in embryonal rhabdomyosarcoma," Cancer cell 24.6 (2013): 710-724.

Clayton, et al., "A Crucial Role for the p110δ Subunit of Phosphatidylinositol 3-Kinase in B Cell Development and Activation," J Exp Med. 2002, 196(6):753-63.

Collins et al., "Rituximab treatment of fibrillary glomerulonephritis," Am J Kidney Dis., 2008, 52(6):1158-62.

Coughlin et al., Approaches and limitations of phosphatidylinositol-3-kinase pathway activation status as a predictive biomarker in the clinical development of targeted theraphy, Breast Cancer Res Treatment, 2010, 124:1-11.

Courtney et al., "The PI3K Pathway as Drug Target in Human Cancer," J Clinc Oncol., 2010, 29:1075-1083.

Crabbe, "The PI3K inhibitor arsenal: choose your weapon!" Trends Biochem Sci., 2007, 32(10):450-56.

Dagia et al., A preferential p110α/γ PI3K inhibitor attenuates experimental inflammation by suppressing the production of proinflammatory mediators in a NF-κB-dependent manner, Am J Physiol— Cell Physiol., 2010, 298:929-941.

DeBerardinis et al., "The Biology of Cancer: Metabolic Reprogramming Fuels Cell Growth and Proliferation," Cell Metabolism, Jan. 2008, 7:11-20.

Delmas and Meunier, "The Management of Paget's Disease of Bone," N Engl J Med., 1997, 336:558-566.

Devauchelle-Pensec, "Treatment of Primary Sjogren Syndrome with Rituximab," Annal Internal Med., 2014, 160:233-242.

Dolezal et al., "Preparation and biological activity of 6-benzylaminopurine derivatives in plants and human cancer cells," *Bioorganic & Medicinal Chemistry* (2006), 14(3), 875-884.

Dolezal et al., "Preparation, biological activity and endogenous occurrence of N6-benzyladenosines," *Bioorganic & Medicinal Chemistry* (2007), 15(11), 3737-3747.

Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.

Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.

Dushianthan et al., "Acute respiratory distress syndrome and acute lung injury," Post Graduate Med J., 2011, 87:612-622.

Engelman, "Targeting PI3K signalling in cancer: opportunities, challenges and limitations," Nature Rev: Cancer, 2009, 9:550-562.

Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).

Fine et al., "Neoplasms of the Central Nervous System," Cancer Principles Practice Oncol., 2005, 2:1834-1887.

Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.

Floberg et al., "Extractive alkylation of 6-mercaptopurine and determination in plasma by gas chromatography-mass spectrometry," *Journal of Chromatography, Biomedical Applications*, (1981), 225(1), 73-81.

Fruman and Bismuth, "Fine Tuning the Immune Response with PI3K," *Immunological Revs.*, 2006, 228:253-272.

Garvey, "Rituximab in the treatment of autoimmune haematolgoical disorders," British Journal of Haematology, 2008, 141: 149-169.

(56) References Cited

OTHER PUBLICATIONS

Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Ghigo et al., "PI3K inhibition in inflammation: Toward tailored therapies for specific diseases," BioEssays, 2010, 32:185-196.
Godeau et al., "Rituximab efficacy and safety in adult splenectomy candidates with chronic immune thrombocytopenic purpura: results of a prospective multicenter phase 2 study," Blood, 2008, 112(4):999-1004.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999)*Too Voluminous to Provide.
Wuts and Greene, Protective Groups in Organic Synthesis, 4th ed., John Wiley & Sons: New Jersey, pp. 696-887,2007.
Harley, "Medical Management of Actue Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.
Hayter and Cook, "Updated assessment of the prevalence, spectrum and case definition of autoimmune disease," Autoimmunity Reviews, 2012, 11:754-765.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents I Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al., "Inhibitors of phosphatidylinositol-3-kinase in cancer therapy", *Molecular Aspects of Medicine*, 31(2):135-144, 2010.
Irie, et al., "Discovery of selective and nonpeptidic cathepsin S inhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.
Japanese Office Action in Japanese Application No. 2014-528654, dated Mar. 29, 2016, 5 pages (English Translation).
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian *Aplidiopsis* sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.
Kim et al., "A signaling network in Phenylephrine-Induced Benign Prostatic Hyperplasia," Endocrinology, 2009, 150:3576-3583.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes PIK3CA and PIKE in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kong and Yamori, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," *Bioorganic & Medicinal Chemistry Letters* (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.
Kuster (ed), Kinase Inhibitors: Methods and Protocols Methods in Molecular Biology, 2012, 795:1-44.

(56) References Cited

OTHER PUBLICATIONS

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al., "Inhibition of phosphoinositide 3-kinase δ attenuates allergic airway inflammation and hyperresponsiveness in murine asthma model," FASEB J. 2006, 20(3):455-65.

Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Optimization of the heterocyclic core of the quinazolinone-derived CXCR3 antagonists," *Bioorganic & Medicinal Chemistry Letters* (2008), 18(2), 688-693.

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus:an autoimmune disease of B cell hyperactivity," Nat Immunol., 2001, 2(9):764-6.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lovric et al., "Rituximab as rescue therapy in anti-neutrophil cytoplasmic antibody-associated vasculitis: a single-centre expereince with 15 patients," Nephrol Dial Transplant, 2009, 24: 179-185.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga *Rhodomela confervoides*", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3- d]pyrimidines," *European Journal of Medicinal Chemistry* (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=142974298438809105451304289684>. 10 pages.

Meijer et al., "Treatment of primary Sjögren syndrome with rituximab: extended follow-up, safety and efficacy of retreatment," Ann. Rheum. Dis., 68(2):284-285, 2009.

Medeot et al., "Rituximab therapy in adult patients with relapsed or refractory immune thrombocytopenic purpura: long-term follow-up results," European Journal of Haematology, 2008, 81: 165-169.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society*, Perkin Transactions 1 (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, *Chemistry Letters* (2001), (10), 1064-1065.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors , a review of the patent literature", Expert Opinion on Therapeutic Patents, Informa Healthcare, 21(11):1773-1790, 2011.

(56) References Cited

OTHER PUBLICATIONS

Oki, et al., "Reactivities of Stable Rotamers. XLII. Generation and Fates of Rotameric [1-(9Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., Analytical Biochemistry 1999, 269, 94-104.
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals "0 *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93, Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxide elimination," *Organic Reactions* (Hoboken, NJ, United States) (1993), 44, No pp. given.
Remington's Pharmaceutical Sciences, 17th ed., Mack Publishing Company, Easton, Pa., 1985, p. 1418.
Ringshausen et al, "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Oncogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Selig et al., "The application of Stille cross-coupling reactions with multiple nitrogen containing heterocycles," Tetrahedron, Sep. 2011, 67(47): 9204-9213.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elselvier. Northwestern University. Second Edition. Evanstons Illinois. 2004. p. 29 and table 2.2 *Too Voluminous to Provide.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," *J Immunol.*, 2009, 183:6472-3480.
Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.

(56) References Cited

OTHER PUBLICATIONS

Walsh and Jayne, "Rituximab in the treatment of anti-neutrophil cytoplasm antibody associated vasculitis and systemic lupus erythematosis: past, present and future," Kidney International, 2007, 72: 676-682.
Wang et al., "Anticancer drugs of phosphatidylinositol 3 kinase inhibitors," World Notes on Antibiotics, Dec. 2008, 29(5): 206-212.
WebMD. Arthritis Health Center: What is Inflammation? Jul. 6, 2012, www.webmd.com/arthritis/about-inflammation?page=2, 4 pages.
WebMD. Bladder Cancer Health Center: Bladder Cancer-Prevention, Apr. 30, 2013, www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?page=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
Xu et al "Activation of the PI3K/AKT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-1-benzyl-4-cyanoimiclazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41: 5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, dated Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
Office Action in CO Application No. 11-179.464, dated Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
Canadian Examination Report in Canadian Application No. 2,766,100, dated Jan. 31, 2017, 3 pages.

(56) References Cited

OTHER PUBLICATIONS

International Preliminary Report on Patentability in International Application No.PCT/US2015/035046, dated Dec. 22, 2016, 7 pages.
Malaysian Office Action in Malaysian Application No. PI 2011006255, dated Mar. 15, 2017, 2 pages.
European Search Report in European Application No. 16199883.6, dated Jun. 4, 2017, 7 pages.
Taiwan Office Action in Taiwan Application No. 105111882, dated Mar. 8, 2017, 5 pages (English Translation).
Vietnamese Office Action in Vietnamese Application No. 2012-00241, dated May 9, 2017, 3 pages (English Translation).
International Preliminary Report on Patentability in International Application No. PCT/US2016/019741, dated Aug. 29, 2017, 10 pages.
Vietnamese Office Action in Vietnamese Application No. 2017-03601, dated Nov. 27, 2017, 2 pages (English Translation).
International Preliminary Report on Patentability in International Application No. PCT/US2016/031606, dated Nov. 23, 2017, 7 pages.
International Preliminary Report on Patentability in International Application No. PCT/US2016/031611, dated Nov. 23, 2017, 7 pages.
International Preliminary Report on Patentability in International Application No. PCT/US2016/031603, dated Nov. 23, 2017, 7 pages.
Costa Rican Office Action in Costa Rican Application No. 2014-111, dated Nov. 8, 2018, 7 pages.
Chilean Opposition in Chilean Application No. 2179-2017, dated Oct. 2, 2018, 10 pages.
Columbian Office Action in Columbian Application No. NC2017/0008924, dated Nov. 21, 2018, 10 pages.

* cited by examiner

SALTS AND PROCESSES OF PREPARING A PI3K INHIBITOR

This application claims the benefit of U.S. Ser. No. 62/121,697, filed Feb. 27, 2015, which is incorporated herein by reference in its entirety.

TECHNICAL FIELD

The present application provides process for preparing (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one, which is useful as an inhibitor of phosphoinositide 3-kinase-delta (PI3Kδ), as well as a salt form and intermediates related thereto.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate (PIP2) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455): 1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur. J. Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011): 1007-11; Lee, et al., FASEB J. 2006, 20(3):455-65) and to have attenuated disease in a model of RA (Randis, et al., Eur. J. Immunol., 2008, 38(5):1215-24).

B cell proliferation has shown to play a major role in the development of inflammatory autoimmune diseases (Puri, Frontiers in Immunology (2012), 3(256), 1-16; Walsh, Kidney International (2007) 72, 676-682). For example, B cells support T-cell autoreactivity, an important component of inflammatory autoimmune diseases. Once activated and matured, B cells can traffic to sites of inflammation and recruit inflammatory cells or differentiate to plasmablasts. Thus, activity of B-cells can be affected by targeting B-cell stimulatory cytokines, B-cell surface receptors, or via B-cell depletion. Rituximab—an IgG1 κ mouse/human chimeric monoclonal antibody directed against the B-cell surface receptor CD20—has been shown to deplete CD20+ B cells. Use of rituximab has been shown to have efficacy in treating idiopathic thrombocytopenic purpura, autoimmune hemolytic anemia, or vasculitis. For example, treatment with rituximab resulted in remission of the disease in patients suffering from anti-neutrophil cytoplasm antibody associated (ANCA) systemic vasculitis (AASV) with demonstrated peripheral B-cell depletion (Walsh, 2007; Lovric, Nephrol Dial Transplant (2009) 24: 179-185). Similarly, a complete response was reported in one-third to two-thirds of patients having mixed cryoglobulinemia vasculitis after treatment with rituximab, including patients who presented with a severe form of vasculitis that was resistant or intolerant to other treatments (Cacoub, Ann Rheum Dis 2008; 67:283-287). Similarly, rituximab has been shown to have efficacy in treating patients with idiopathic thrombocytopenic purpura (or immune thrombocytopenic purpura) (Garvey, British Journal of Haematology, (2008) 141, 149-169; Godeau, Blood (2008), 112(4), 999-1004; Medeo, European Journal of Haematology, (2008) 81, 165-169) and autoimmune hemolytic anemia (Garvey, British Journal of Haematology, (2008) 141, 149-169).

PI3Kδ signaling has been tied to B cell survival, migration, and activation (Puri, *Frontiers in Immunology,* 2012, 3(256), 1-16, at pages 1-5; and Clayton, *J Exp Med,* 2002, 196(6):753-63). For example, PI3Kδ is required for antigen-dependent B-cell activation driven by B cell receptor. By blocking B-cell adhesion, survival, activation, and proliferation, PI3Kδ inhibition can impair the ability of B cells to activate T cells, preventing their activation and reducing secretion of autoantibodies and pro-inflammatory cytokines. Hence, by their ability to inhibit B cell activation, PI3Kδ inhibitors would be expected to treat B cell mediated diseases that were treatable by similar methods such as B cell depletion by rituximab. Indeed, PI3Kδ inhibitors have been shown to be useful mouse models of various autoimmune diseases that are also treatable by rituximab such as arthritis (Puri (2012)). Further, innate-like B cells, which are linked to autoimmunity are sensitive to PI3Kδ activity, as MZ and B-1 cells are nearly absent in mice lacking the p110δ gene (Puri (2012). PI3Kδ inhibitors can reduce trafficking of and activation of MZ and B-1 cells, which are implicated in autoimmune diseases.

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol. Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

For these reasons, there is a need to develop new PI3K inhibitors that can be used inflammatory disorders, autoimmune diseases and cancer. This invention is directed to this need and others.

SUMMARY

The present application provides processes of preparing a compound of Formula I:

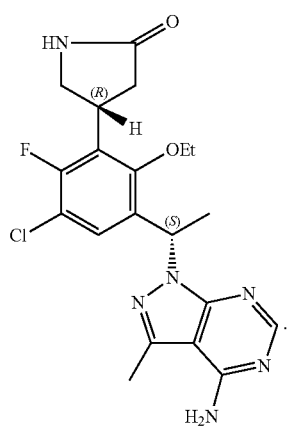

or a pharmaceutically acceptable salt thereof, which is useful as an inhibitor of PI3Kδ.

The present application further provides a hydrochloric acid salt of the compound of Formula I.

The present application also provides pharmaceutical compositions comprising a hydrochloric acid salt described herein and a pharmaceutically acceptable carrier.

The present application further provides methods of inhibiting an activity of a PI3K kinase, comprising contacting the kinase with the hydrochloric acid salt of the compound of Formula I.

The present application also provides methods of treating a disease in a patient, wherein said disease is associated with abnormal expression or activity of a PI3K kinase, comprising administering to said patient a therapeutically effective amount of the hydrochloric acid salt of the compound of Formula I.

The present application additionally provides the hydrochloric acid salt of the compound of Formula I for use in any of the methods described herein.

The present application further provides use of the hydrochloric acid salt of the compound of Formula I for the manufacture of a medicament for use in any of the methods described herein.

The present application also provides a process of preparing the hydrochloric acid salt of the compound of Formula I, comprising reacting a compound of Formula I:

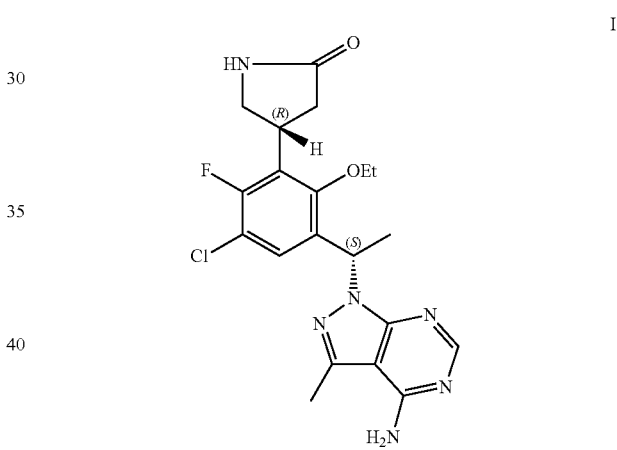

with hydrochloric acid to form said salt.

The present application additionally provides a process of preparing a compound of Formula I, comprising reacting a compound of Formula XVI:

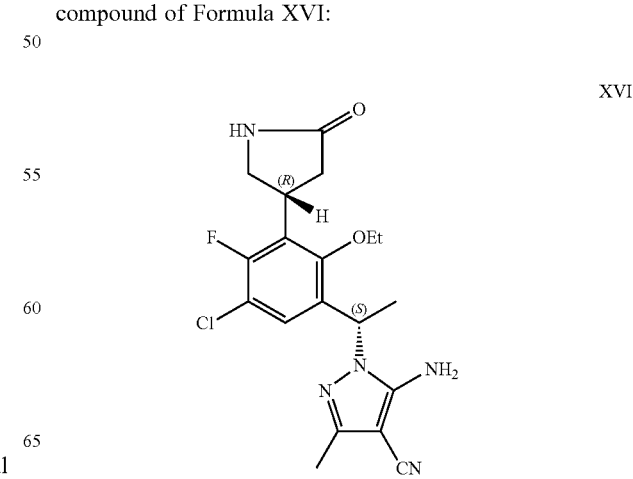

with formamidine acetate to form said compound of Formula I:

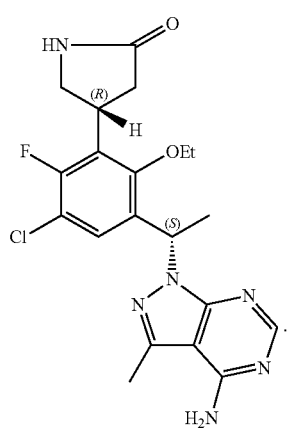

The present application further provides a compound of Formula XIV:

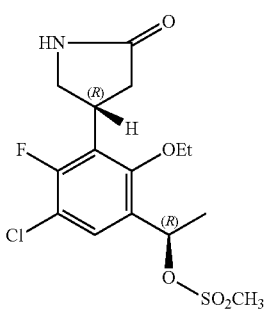

or a pharmaceutically acceptable salt thereof.

The present application also provides a compound of Formula XV:

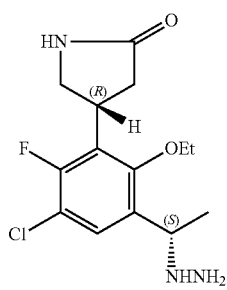

or a pharmaceutically acceptable salt thereof.

The present application additionally provides a compound of Formula XVI:

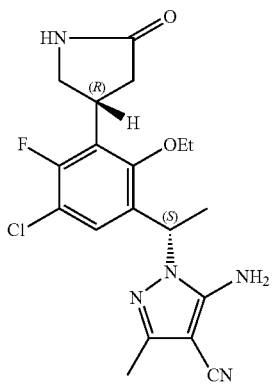

or a pharmaceutically acceptable salt thereof.

The present application further provides a compound of Formula XIX:

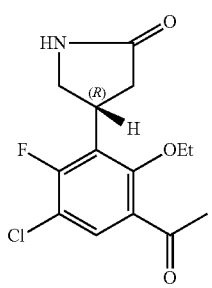

or a pharmaceutically acceptable salt thereof.

The present application also provides a compound of Formula XX:

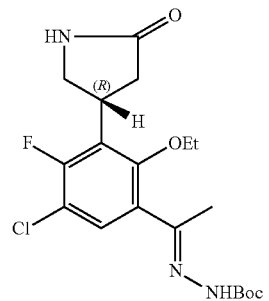

or a pharmaceutically acceptable salt thereof.

The present application additionally provides a compound of Formula XXI:

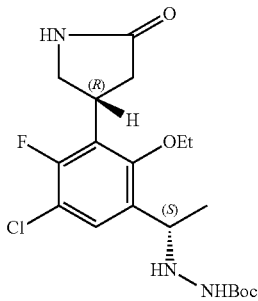

XXI or a pharmaceutically acceptable salt thereof.

DETAILED DESCRIPTION

Compounds and Salts

Figure 1:
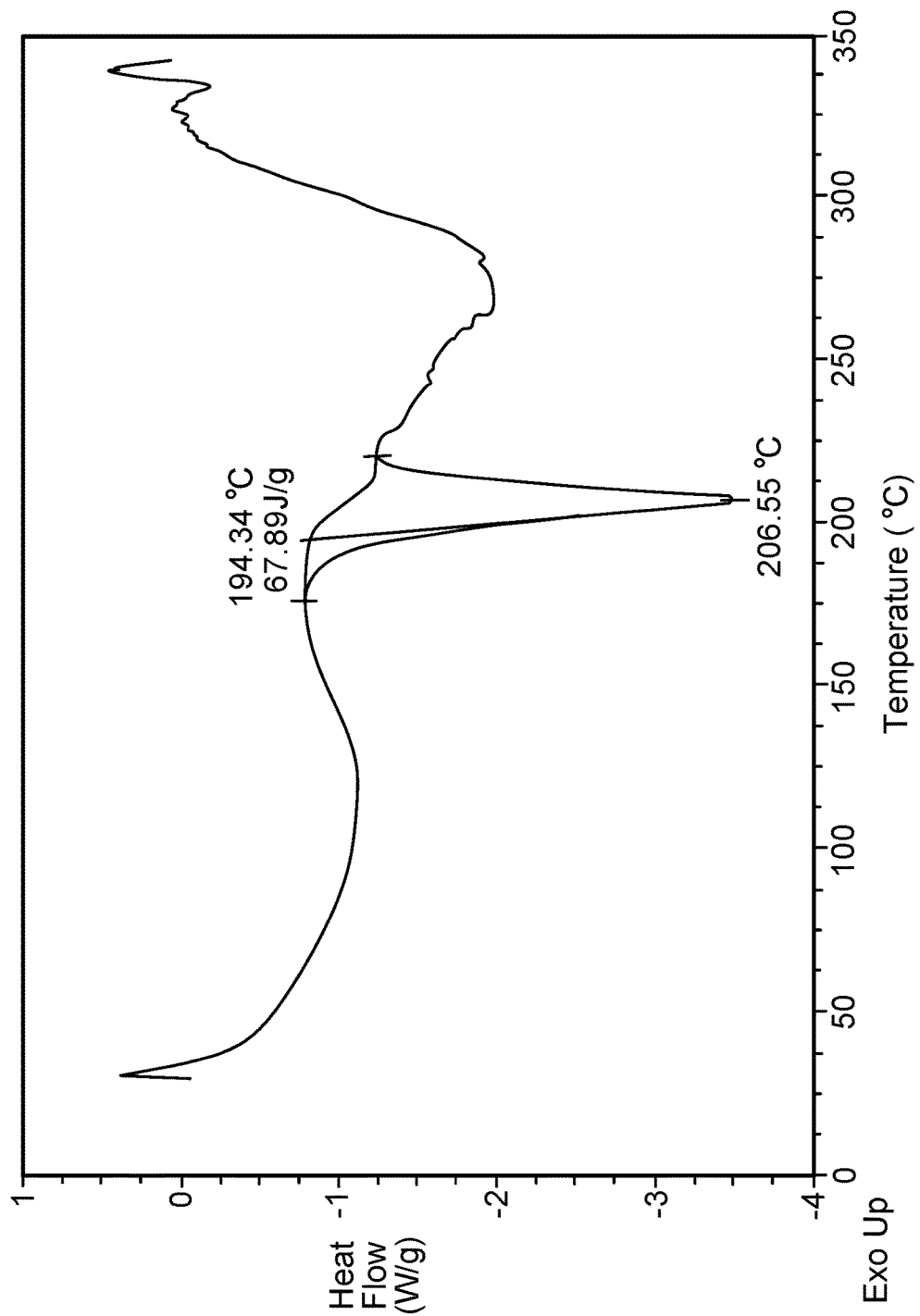
FIG. 1 shows a DSC thermogram representative of the salt of Example 3.

The present application provides processes of preparing a compound of Formula I:

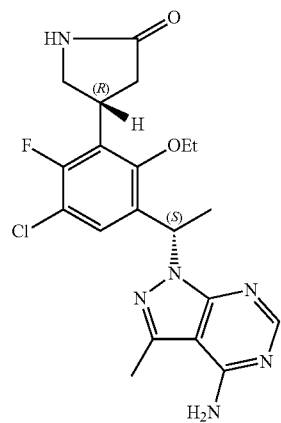

I or a pharmaceutically acceptable salt thereof, which is useful as an inhibitor of PI3Kδ, wherein Et is ethyl.

The present application further provides a salt of the compound of Formula I.

Accordingly, in some embodiments, the present application provides 4-(3-(1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt. In some embodiments, the present application provides (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt. In some embodiments, the salt is a 1:1 stoichiometric ratio of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one to hydrochloric acid.

Different forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

In some embodiments, the hydrochloric acid salt of the compound of Formula I provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different salt forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

Figure 3:
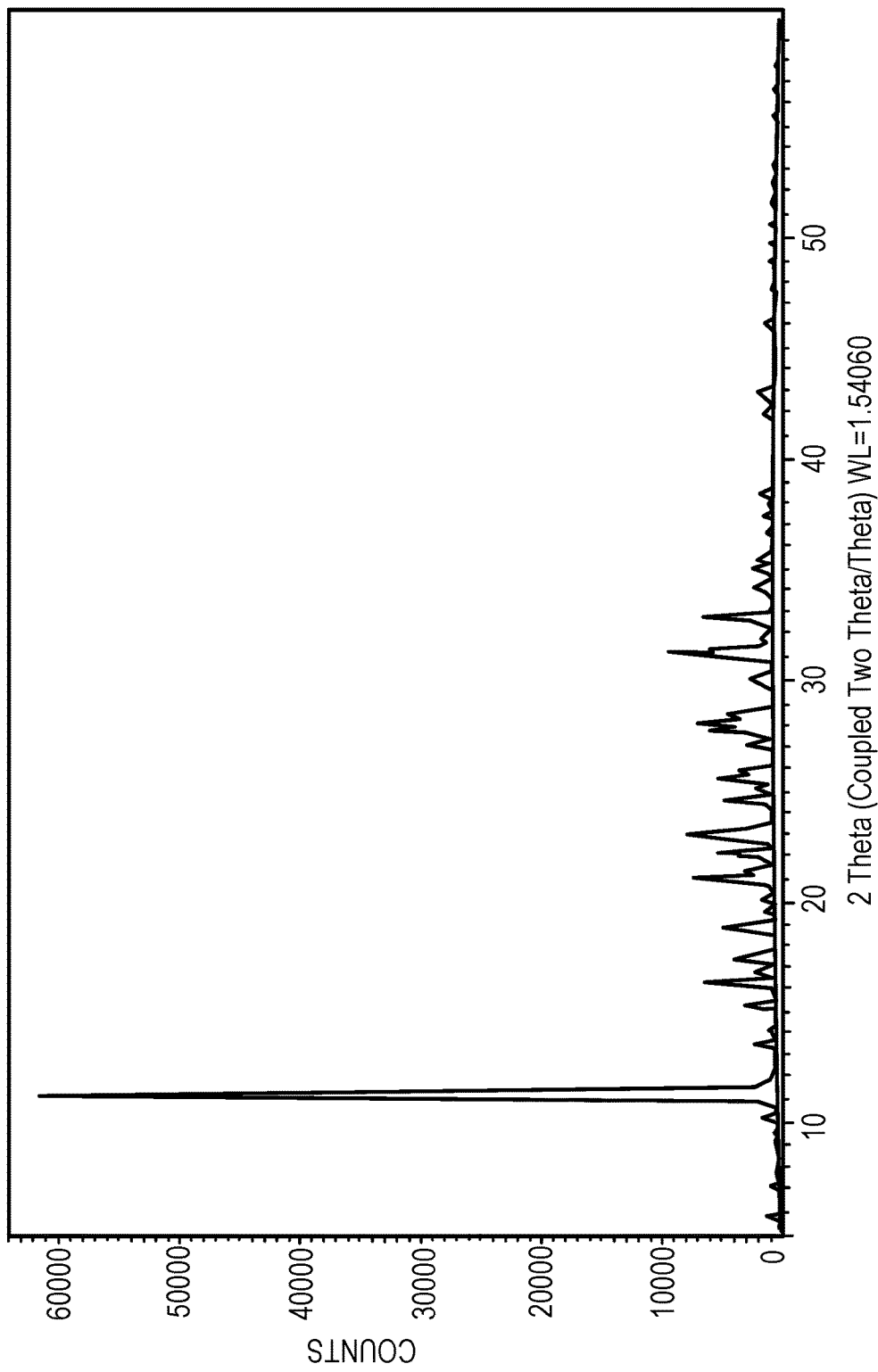
FIG. 3 shows an XRPD pattern representative of the salt of Example 3.

In some embodiments, the hydrochloric acid salt of the compound of Formula I has at least one XRPD peak, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has at least two XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has at least three XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has at least four XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has at least five XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has an XRPD profile substantially as shown in FIG. 3.

Figure 2:
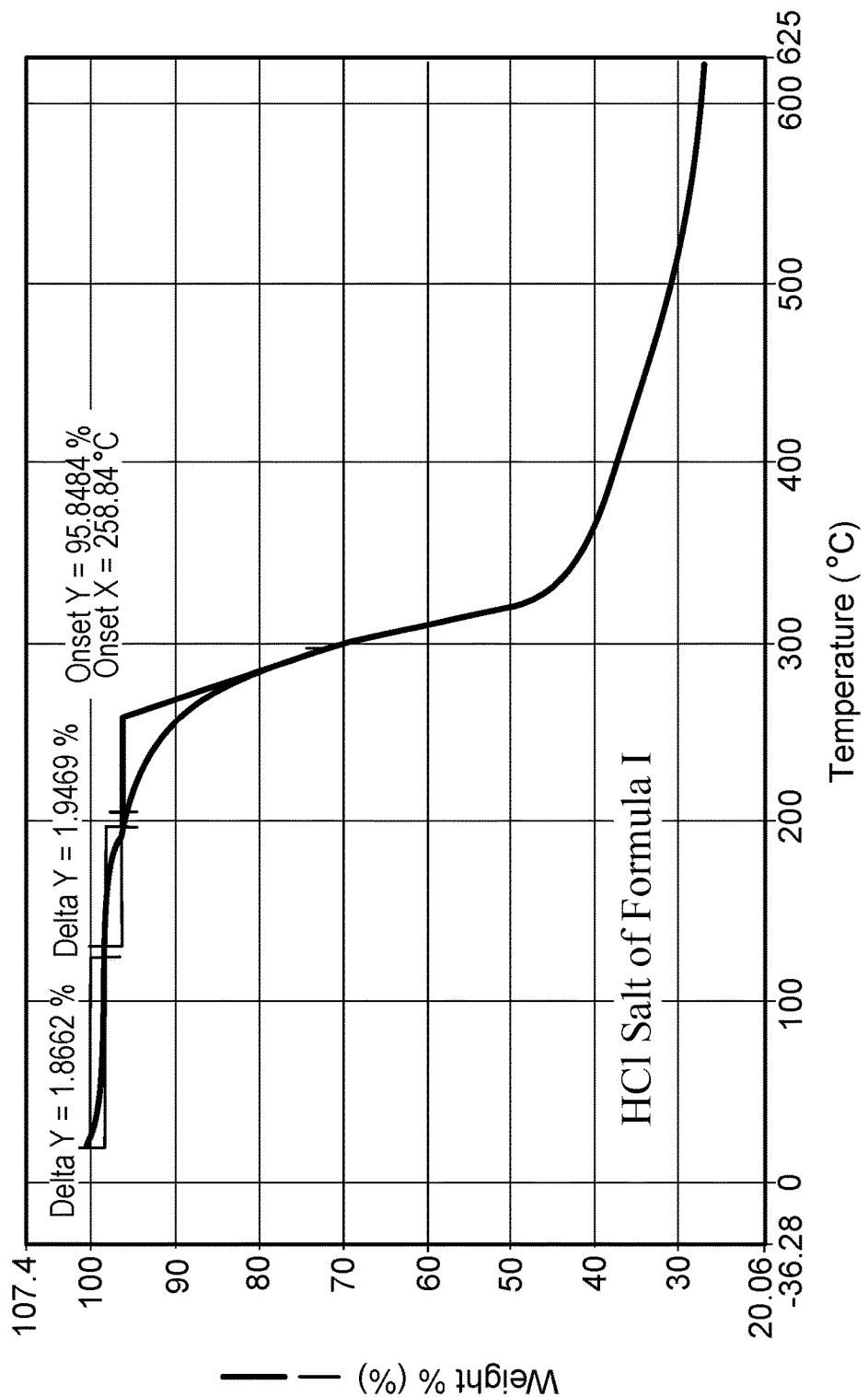
FIG. 2 shows TGA data representative of the salt of Example 3.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation. In some embodiments, the hydrochloric acid salt of the compound of Formula I has a DSC thermogram having an endothermic peak at about 207° C. In some embodiments, the hydrochloric acid salt of the compound of Formula I has a DSC thermogram substantially as shown in FIG. 1. In some embodiments, the hydrochloric acid salt of the compound of Formula I has a TGA thermogram substantially as shown in FIG. 2.

In some embodiments, the salts and compounds described herein (e.g., the compound of Formula I or the hydrochloric acid salt of the compound of Formula I) are substantially isolated. By "substantially isolated" is meant that the salt or compound is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating compounds and their salts are routine in the art.

Intermediates

The present application further provides intermediates that are useful in the preparation of the compound of Formula I.

Accordingly, in some embodiments, the present application provides a compound of Formula XIV:

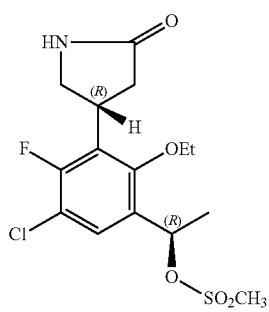

XIV or a pharmaceutically acceptable salt thereof.

The present application further provides a compound of Formula XV:

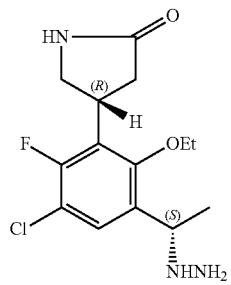

XV or a pharmaceutically acceptable salt thereof.

The present application further provides a compound of Formula XVI:

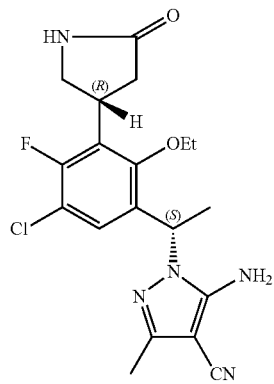

XVI or a pharmaceutically acceptable salt thereof.

The present application further provides a compound of Formula XIX:

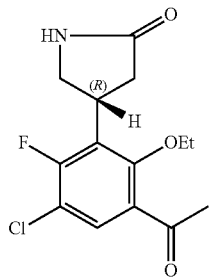

XIX or a pharmaceutically acceptable salt thereof.

The present application further provides a compound of Formula XX:

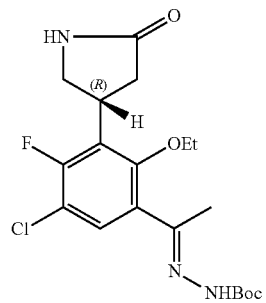

XX or a pharmaceutically acceptable salt thereof.

The present application further provides a compound of Formula XXI:

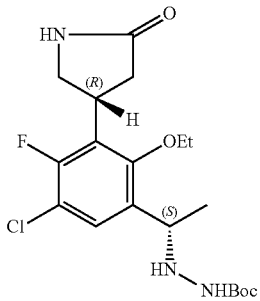

or a pharmaceutically acceptable salt thereof.

Processes

The present application further provides a process of preparing a salt of Formula I:

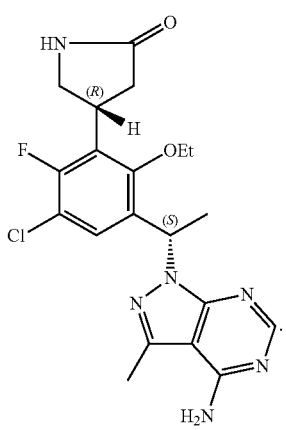

In some embodiments, the process comprises reacting a compound of Formula I:

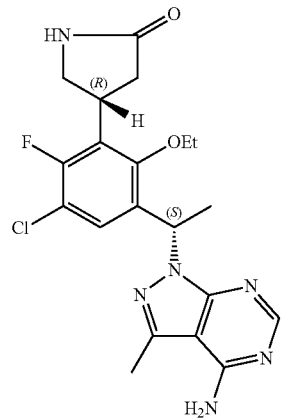

with hydrochloric acid to form said salt.

In some embodiments, said hydrochloric acid is 1 M aqueous hydrochloric acid.

In some embodiments, about 3.3 to about 3.7 equivalents of hydrochloric acid is used based on 1 equivalent of the compound of Formula I.

In some embodiments, said reacting is performed at a temperature of from about 45° C. to about 55° C.

In some embodiments, the process comprises:
adding hydrochloric acid to the compound of Formula I at room temperature to form a slurry;
heating said slurry to a temperature of from about 45° C. to about 55° C. to form a solution; and
cooling the solution to a temperature of from about 0° C. to about 5° C. to crystallize said salt.

In some embodiments, the process comprises reacting a compound of Formula XVI:

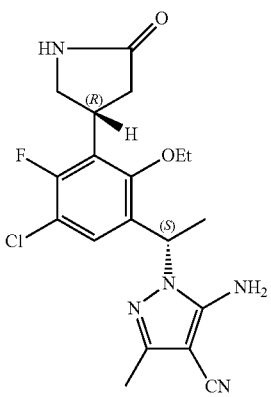

with formamidine acetate to form a compound of Formula I:

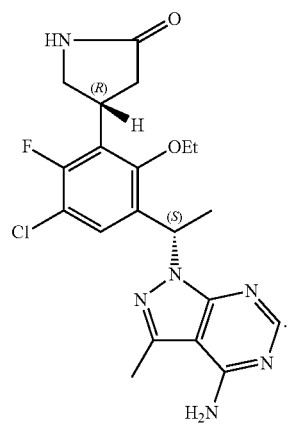

In some embodiments, said reacting of the compound of Formula XVI with formamidine acetate is conducted in a solvent component comprising 1,2-ethanediol.

In some embodiments, said reacting of the compound of Formula XVI with formamidine acetate is performed at a temperature of from about 100° C. to about 105° C.

In some embodiments, about 8 to about 10 equivalents of formamidine acetate is used based on 1 equivalent of the compound of Formula XVI.

In some embodiments, the process further comprises preparing the compound of Formula XVI by a process comprising reacting a compound of Formula XV:

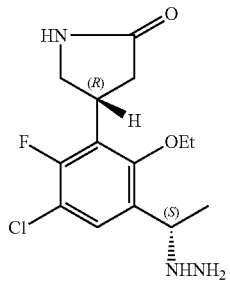

XV with (1-ethoxyethylidene)malononitrile in the presence of a tertiary amine.

In some embodiments, said tertiary amine is N-methylpyrrolidinone.

In some embodiments, said reacting of the compound of Formula XV with (1-ethoxyethylidene)malononitrile is performed at about room temperature.

In some embodiments, the process further comprises preparing the compound of Formula XV by a process comprising reacting a compound of Formula XIV-a:

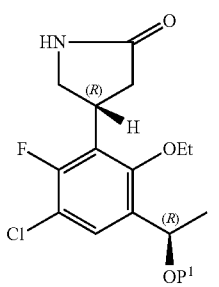

XIV-a with hydrazine in the presence of a tertiary amine, wherein $P^1$ is $C_{1-6}$ alkylsulfonyl.

In some embodiments, said tertiary amine is N-methylpyrrolidinone.

In some embodiments, said reacting of the compound of Formula XIV-a with hydrazine is performed at a temperature of from about 35° C. to about 60° C.

In some embodiments, said reacting of the compound of Formula XIV-a with hydrazine is conducted in a solvent component comprising dichloromethane.

In some embodiments, $P^1$ is methanesulfonyl group.

In some embodiments, the process further comprises preparing the compound of Formula XIV by a process comprising reacting a compound of Formula XIII:

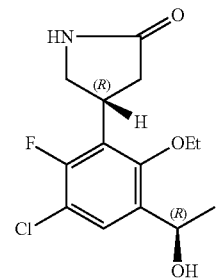

XIII with $C_{1-6}$ alkylsulfonylhalide in the presence of a tertiary amine.

In some embodiments, said $C_{1-6}$ alkylsulfonylhalide is methanesulfonyl chloride.

In some embodiments, said tertiary amine is N,N-diisopropylethylamine.

In some embodiments, about 1.1 to about 1.5 equivalents of alkylsulfonylhalide is used based on 1 equivalent of the compound of Formula XIII.

In some embodiments, said reacting of said compound of Formula XIII with $C_{1-6}$ alkylsulfonylhalide is performed at a temperature of from about −10° C. to about 5° C.

In some embodiments, said reacting of said compound of Formula XIII with $C_{1-6}$ alkylsulfonylhalide is performed in a solvent component comprising dichloromethane.

In some embodiments, the steps of: (i) reacting of said compound of Formula XIII with $C_{1-6}$ alkylsulfonylhalide; (ii) reacting said compound of Formula XIV-a with hydrazine in the presence of a tertiary amine to form a compound of Formula XV; and (iii) reacting said compound of Formula XV with formamidine acetate to form a compound of Formula XVI are conducted in the same pot without isolation of the compound of Formula XIV-a or the compound of Formula XV.

In some embodiments, the process further comprises preparing the compound of Formula XVI by a process comprising reacting a salt of Formula XV-a:

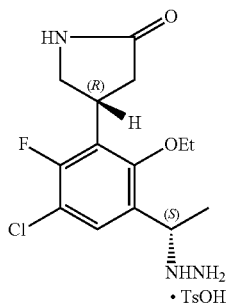

XV-a with (1-ethoxyethylidene)malononitrile in the presence of a tertiary amine, wherein TsOH is p-toluenesulfonic acid.

In some embodiments, said tertiary amine is N,N-diisopropylethylamine.

In some embodiments, said reacting a salt of Formula XV-a with (1-ethoxyethylidene)malononitrile is performed at about room temperature.

In some embodiments, about 1.3 to about 1.6 equivalents of (1-ethoxyethylidene)malononitrile is used based on 1 equivalent of the salt of Formula XV-a.

In some embodiments, said reacting of the salt of Formula XV-a with (1-ethoxyethylidene)malononitrile is conducted in a solvent component comprising ethanol.

In some embodiments, the process further comprising preparing the salt of Formula XV-a by a process comprising reacting a compound of Formula XXI:

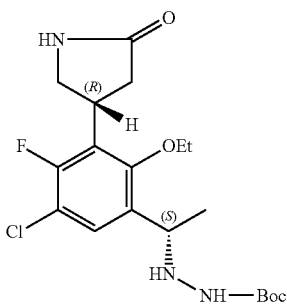

XXI with p-toluenesulfonic acid, wherein Boc is tert-butoxycarbonyl.

In some embodiments, said p-toluenesulfonic acid is p-toluenesulfonic acid monohydrate.

In some embodiments, about 1.3 to about 1.6 equivalents of p-toluenesulfonic acid is used based on 1 equivalent of the compound of Formula XXI.

In some embodiments, said reacting of said compound of Formula XXI with p-toluenesulfonic acid is performed at a temperature of from about 45° C. to about 65° C.

In some embodiments, reacting of said compound of Formula XXI with p-toluenesulfonic acid is conducted in a solvent component comprising ethanol.

In some embodiments, the steps of: (i) reacting said compound of Formula XXI with p-toluenesulfonic acid to form a salt of Formula XV-a; and (ii) reacting said salt of Formula XV-a with (1-ethoxyethylidene)malononitrile are conducted in the same pot without isolation of the salt of Formula XV-a.

In some embodiments, the process further comprises preparing the compound of Formula XXI by a process comprising reacting a compound of Formula XX:

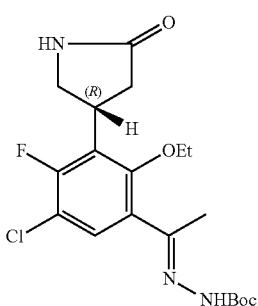

XX with hydrogen gas in the presence of one or more independently selected hydrogenation catalysts, wherein Boc is tert-butoxycarbonyl.

In some embodiments, said reacting of the compound of Formula XX with hydrogen gas is performed in the presence of two independently selected hydrogenation catalysts.

In some embodiments, one hydrogenation catalyst is bis(1,5-cyclooctadiene)rhodium(I)tetrafluoroborate and the other is (R)-(-)-1-{(S)-2-[bis(4-trifluoromethylphenyl)phosphine]ferrocenyl}ethyl-di-t-butylphosphine.

In some embodiments, about 13.5 to about 14.5 equivalents of bis(1,5-cyclooctadiene)rhodium(I)tetrafluoroborate is used based on 1 equivalent of the compound of Formula XX.

In some embodiments, about 12 to about 13 equivalents of (R)-(-)-1-{(S)-2-[bis(4-trifluoromethylphenyl)phosphine]ferrocenyl}ethyl-di-t-butylphosphine is used based on 1 equivalent of the compound of Formula XX.

In some embodiments, said reacting of the compound of Formula XX with hydrogen gas is performed at about room temperature.

In some embodiments, said reacting of the compound of Formula XX with hydrogen gas is conducted in a solvent component comprising methanol.

In some embodiments, the process further comprises preparing the compound of Formula XX by a process comprising reacting a compound of Formula XIX:

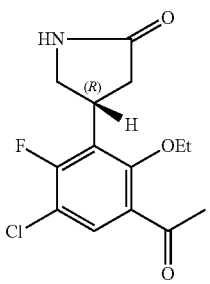

XIX with t-butyl carbazate.

In some embodiments, said reacting of the compound of Formula XIX with t-butyl carbazate is performed at a temperature of from about 60° C. to about 70° C.

In some embodiments, said reacting of the compound of Formula XIX with t-butyl carbazate is conducted in a solvent component comprising methanol.

In some embodiments, the process further comprises preparing the compound of Formula XIX by a process comprising oxidizing a compound of Formula XIII-a:

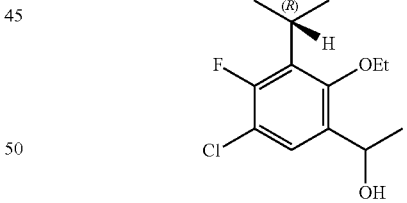

XIII-a in the presence of an oxidizing agent.

In some embodiments, said oxidizing agent is Dess-Martin periodinane.

In some embodiments, about 1.2 to about 1.7 equivalents of said oxidizing agent is used based on 1 equivalent of the compound of Formula XIII-a.

In some embodiments, said oxidizing of the compound of Formula XIII-a is performed at about room temperature.

In some embodiments, said oxidizing of the compound of Formula XIII-a is conducted in a solvent component comprising dichloromethane.

In some embodiments, said compound of Formula XIII is prepared by a process comprising heating a compound of Formula XII:

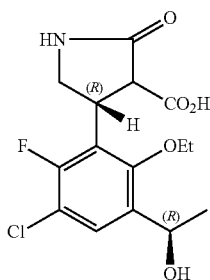

in the presence of a solvent component.

In some embodiments, said heating is performed at a temperature of from about 95° C. to about 105° C.

In some embodiments, said solvent component comprises 1,4-dioxane.

In some embodiments, said solvent component comprises toluene.

In some embodiments, said solvent component comprises 1,4-dioxane and toluene.

In some embodiments, said compound of Formula XII is prepared by a process comprising reacting a compound of Formula XI:

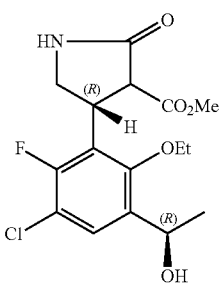

in the presence of a strong base.

In some embodiments, said strong base is sodium hydroxide.

In some embodiments, said strong base is 1 M aqueous sodium hydroxide.

In some embodiments, said reacting is performed at about room temperature.

In some embodiments, said compound of Formula XI is prepared by a process comprising reacting a compound of Formula X:

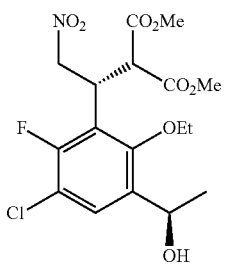

with hydrogen gas in the presence of Raney nickel.

In some embodiments, said reacting is performed at a temperature of from about 50° C. to about 70° C.

In some embodiments, said compound of Formula X is prepared by a process comprising reacting a compound of Formula IX:

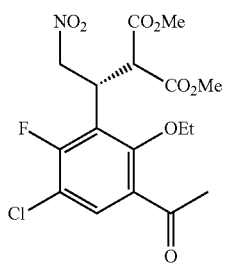

in the presence of boron trifluoride etherate, (3aS)-1-methyl-3,3-diphenyltetrahydro-3H-pyrrolo[1,2-c][1,3,2]oxazaborole ((S)-MeCBS) catalyst, and a borane complex.

In some embodiments, about 0.03 to about 0.07 equivalents of boron trifluoride etherate is used based on 1 equivalent of the compound of Formula IX.

In some embodiments, about 0.05 to about 0.15 equivalents of (3aS)-1-methyl-3,3-diphenyltetrahydro-3H-pyrrolo[1,2-c][1,3,2]oxazaborole ((S)-MeCBS) catalyst is used based on 1 equivalent of the compound of Formula IX.

In some embodiments, said borane complex is 1.0 M borane-THF complex in THF.

In some embodiments, about 0.9 to about 1.1 equivalents of borane complex is used based on 1 equivalent of the compound of Formula IX.

In some embodiments, said reacting is performed at about room temperature.

In some embodiments, said compound of Formula IX is prepared by a process comprising reacting a compound of Formula VIII:

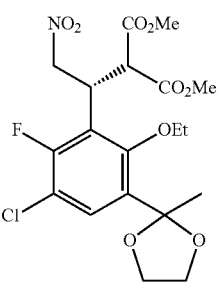

with iodine in the presence of a solvent component.

In some embodiments, said solvent component comprises acetone.

In some embodiments, about 0.75 to about 1.25 equivalents of iodine is used based on 1 equivalent of the compound of Formula VIII.

In some embodiments, said compound of Formula VIII is prepared by a process comprising reacting a compound of Formula VII:

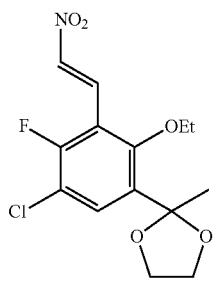

VII with dimethyl malonate in the presence of a catalyst.

In some embodiments, said catalyst is (1S,2S)-N,N'-dibenzylcyclohexane-1,2-diamine-dibromonickel (Evans' Catalyst).

In some embodiments, about 1.1 to about 1.3 equivalents of dimethyl malonate is used based on 1 equivalent of the compound of Formula VII.

In some embodiments, about 0.02 to about 0.03 equivalents of transition metal catalyst is used base on 1 equivalent of the compound of Formula VII.

In some embodiments, said compound of Formula VII is prepared by a process comprising reacting a compound of Formula VI:

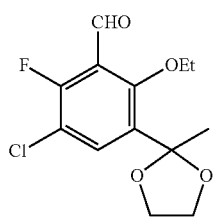

VI with nitromethane in the presence of an organic acid to form a first mixture.

In some embodiments, said organic acid is glacial acetic acid.

In some embodiments, about 9.5 to about 10.5 equivalents of nitromethane is used based on 1 equivalent of the compound of Formula VI.

In some embodiments, said reacting further comprises adding an amine base to said first mixture to form a second mixture.

In some embodiments, said amine base is benzylamine.

In some embodiments, about 0.2 to about 0.3 equivalents of amine base is used based on 1 equivalent of the compound of Formula VI.

In some embodiments, said second mixture is heated at about 55° C. to about 65° C.

In some embodiments, said compound of Formula VI is prepared by a process comprising reacting a compound of Formula V:

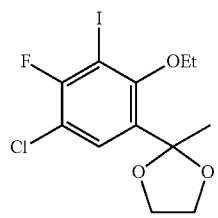

V with a ($C_{1-4}$ alkyl)magnesiumhalide complex to form a first mixture.

In some embodiments, said ($C_{1-4}$ alkyl)magnesium halide complex is 1.3 M isopropylmagnesium chloride lithium chloride complex.

In some embodiments, about 1.1 to about 1.3 equivalents of said ($C_{1-4}$ alkyl)magnesiumhalide complex is used based on 1 equivalent of the compound of Formula V.

In some embodiments, said reacting further comprises adding N-formylmorpholine to said first mixture to form a second mixture.

In some embodiments, about 1.8 to about 2.2 equivalents of N-formylmorpholine is used based on 1 equivalent of the compound of Formula V.

In some embodiments, said reacting is performed at a temperature of from about −5° C. to about 10° C.

In some embodiments, said compound of Formula V is prepared according to procedures described in U.S. Publication No. 2013-0059835A1.

In some embodiments, said compound of Formula VI is prepared by a process comprising reacting a compound of Formula V-a:

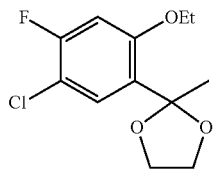

V-a with N,N-dimethylformamide in the presence of lithium diisopropylamide.

In some embodiments, said lithium diisopropylamide is prepared by reacting N,N-diisopropylamine in the presence of n-butyllithium.

In some embodiments, said lithium diisopropylamide is prepared at a temperature of from about −75° C. to about 5° C.

In some embodiments:
(ii) said compound of Formula V-a is reacted with lithium diisopropylamide to form a first mixture; and
(ii) N,N-dimethylformamide is added to said first mixture to form a second mixture.

In some embodiments, about 1.2 to about 1.3 equivalents of amine base is used based on 1 equivalent of the compound of Formula V-a.

In some embodiments, about 1.4 to about 1.6 equivalents of N,N-dimethylformamide is used based on 1 equivalent of the compound of Formula V-a.

In some embodiments, said compound of Formula V-a is prepared by a process comprising reacting a compound of Formula IV-a:

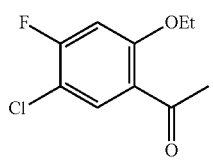

with 1,2-ethanediol in the presence of p-toluenesulfonic acid.

In some embodiments, said p-toluenesulfonic acid is p-toluenesulfonic acid monohydrate.

In some embodiments, about 2.2 to about 2.7 equivalents of 1,2-ethanediol is used based on 1 equivalent of the compound of Formula IV-a.

In some embodiments, about 0.05 to about 0.1 equivalents of p-toluenesulfonic acid is used based on 1 equivalent of the compound of Formula IV-a.

In some embodiments, said reacting is performed at about reflux.

In some embodiments, said compound of Formula IV-a is prepared by a process comprising reacting a compound of Formula II:

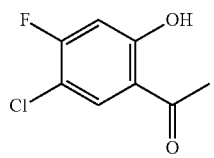

with $CH_2CH_2-X^1$ in the presence of an alkali metal carbonate base, wherein:

$X^1$ is halide.

In some embodiments, $X^1$ is iodide.

In some embodiments, said alkali metal carbonate base is potassium carbonate.

In some embodiments, about 1.1 to about 1.3 equivalents of $CH_2CH_2-X^1$ is used based on 1 equivalent of the compound of Formula II.

In some embodiments, about 1.8 to about 2.2 equivalents of alkali metal carbonate base is used based on 1 equivalent of the compound of Formula II.

In some embodiments, said reacting is performed at about 55° C. to about 65° C.

In some embodiments, said compound of Formula II is prepared according to procedures described in U.S. Publication No. 2013-0059835A1.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

The salts and compounds described herein can be asymmetric (e.g., having one or more stereocenters). If no stereochemistry is indicated, then all stereoisomers, such as enantiomers and diastereomers, are intended unless otherwise indicated by the structure or name. Salts and compounds of the present application that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the salts and compounds described herein, and all such stable isomers are contemplated in the present application. Cis and trans geometric isomers of the salts and compounds of the present application are described and may be isolated as a mixture of isomers or as separated isomeric forms.

Resolution of racemic mixtures of salts and compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Salts and compounds of the invention can also include all isotopes of atoms occurring in the intermediates or final salts or compounds. Isotopes include those atoms having the same atomic number but different mass numbers. For example, isotopes of hydrogen include tritium and deuterium.

In some embodiments, the compounds or salts can be found together with other substances such as water and solvents (e.g. hydrates and solvates) or can be isolated.

In some embodiments, the compounds described herein, or salts thereof (e.g., the hydrochloric acid salt of the compound of Formula I), are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As will be appreciated, the compounds provided herein, including salts thereof, can be prepared using known organic synthesis techniques and can be synthesized according to any of numerous possible synthetic routes. The processes described herein can be monitored according to any suitable method known in the art. For example, product formation can be monitored by spectroscopic means, such as nuclear magnetic resonance spectroscopy (e.g., 1H or 13C), infrared spectroscopy, or spectrophotometry (e.g., UV-visible); or by chromatography such as high performance liquid chromatography (HPLC) or thin layer chromatography (TLC) or other related techniques.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The reactions of the processes described herein can be carried out in air or under an inert atmosphere. Typically, reactions containing reagents or products that are substantially reactive with air can be carried out using air-sensitive synthetic techniques that are well known to the skilled artisan.

Methods of Use

The salts and compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the salts and compounds of the invention can be used in methods of modulating a PI3K by contacting the PI3K with any one or more of the salts, compounds or compositions described herein. In some embodiments, salts and compounds of the present application can act as inhibitors of one or more PI3Ks. In further embodiments, the salts and compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present application is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present salts and compounds bind and/or modulate (e.g., inhibit) include any member of the PI3K family. In some embodiments, the PI3K is PI3Kα, PI3Kβ, PI3Kδ, or PI3Kγ. In some embodiments, the PI3K is PI3Kδ or PI3Kγ. In some embodiments, the PI3K is PI3Kδ. In some embodiments, the PI3K is PI3Kγ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one salt or compound of the invention is used to inhibit the activity of one kinase (e.g., PI3Kδ or PI3Kγ).

In some embodiments, more than one salt or compound of the invention is used to inhibit more than one kinase, such as at least two kinases (e.g., PI3Kδ and PI3Kγ).

In some embodiments, one or more of the salts or compounds is used in combination with another kinase inhibitor to inhibit the activity of one kinase (e.g., PI3Kδ or PI3Kγ).

In some embodiments, one or more of the salts or compounds is used in combination with another kinase inhibitor to inhibit the activities of more than one kinase (e.g., PI3Kδ or PI3Kγ), such as at least two kinases.

The salts and compounds of the invention can be selective. By "selective" is meant that the compound binds to or inhibits a kinase with greater affinity or potency, respectively, compared to at least one other kinase. In some embodiments, the salts and compounds of the invention are selective inhibitors of PI3Kδ or PI3Kγ over PI3Kα and/or PI3Kβ. In some embodiments, the salts and compounds of the invention are selective inhibitors of PI3Kδ (e.g., over PI3Kα, PI3Kβ and PI3Kγ). In some embodiments, the salts and compounds of the invention are selective inhibitors of PI3Kδ (e.g., over PI3Kα, PI3Kβ and PI3Kγ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of salts and compounds of the invention can be determined by cellular assays associated with particular PI3K kinase activity.

Another aspect of the present application pertains to methods of treating a kinase (such as PI3K)-associated disease or disorder in an individual (e.g., patient) by administering to the individual in need of such treatment a therapeutically effective amount or dose of one or more salts or compounds of the present application or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

Further examples of PI3K-associated diseases include idiopathic thrombocytopenic purpura (ITP), autoimmune hemolytic anemia (AIHA), vasculitis, systemic lupus erythematosus, lupus nephritis, pemphigus, membranous nephropathy, chronic lymphocytic leukemia (CLL), Non-Hodgkin lymphoma (NHL), hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the disease is selected from idiopathic thrombocytopenic purpura (ITP), autoimmune hemolytic anemia, vasculitis, systemic lupus erythematosus, lupus nephritis, pemphigus, autoimmune hemolytic anemia (AIHA), membranous nephropathy, chronic lymphocytic leukemia (CLL), Non-Hodgkin lymphoma (NHL), hairy cell leukemia, Mantle cell lymphoma, Burkitt lymphoma, small lymphocytic lymphoma, follicular lymphoma, lymphoplasmacytic lymphoma, extranodal marginal zone lymphoma, Hodgkin's lymphoma, Waldenstrom's macroglobulinemia, prolymphocytic leukemia, acute lymphoblastic leukemia, myelofibrosis, mucosa-associated lymphatic tissue (MALT) lymphoma, B-cell lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS) and B cell lymphoma.

In some embodiments, the method is a method of treating idiopathic thrombocytopenic purpura (ITP) selected from relapsed ITP and refractory ITP.

In some embodiments, the method is a method of treating vasculitis selected from Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, and anti-neutrophil cytoplasm antibody associated (ANCA) systemic vasculitis (AASV).

In some embodiments, the method is a method of treating non-Hodgkin lymphoma (NHL) selected from relapsed NHL, refractory NHL, and recurrent follicular NHL.

In some embodiments, the method is a method of treating B cell lymphoma, wherein said B cell lymphoma is diffuse large B-cell lymphoma (DLBCL).

In some embodiments, the method is a method of treating B cell lymphoma, wherein said B cell lymphoma is activated B-cell like (ABC) diffuse large B cell lymphoma, or germinal center B cell (GCB) diffuse large B cell lymphoma.

In some embodiments, said disease is osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome.

In some embodiments, said disease is rheumatoid arthritis, allergy, asthma, glomerulonephritis, lupus, or inflammation related to any of the aforementioned.

In some embodiments, said lupus is systemic lupus erythematosus or lupus nephritis.

In some embodiments, said disease is breast cancer, prostate cancer, colon cancer, endometrial cancer, brain cancer, bladder cancer, skin cancer, cancer of the uterus, cancer of the ovary, lung cancer, pancreatic cancer, renal cancer, gastric cancer, or a hematological cancer.

In some embodiments, said hematological cancer is acute myeloblastic leukemia or chronic myeloid leukemia.

In some embodiments, said hematological cancer is lymphoid malignancies of B-cell origin including, indolent/aggressive B-cell non-Hodgkin's lymphoma (NHL), and Hodgkin's lymphoma (HL).

In some embodiments, said disease is acute lung injury (ALI) or adult respiratory distress syndrome (ARDS).

As used herein, the term "contacting" refers to the bringing together of indicated moieties in an in vitro system or an in vivo system. For example, "contacting" a PI3K with a compound of the invention includes the administration of a compound of the present application to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the salts or compounds of the present application for treatment of PI3K-associated diseases, disorders or conditions. The one or more additional pharmaceutical agents can be administered to a patient simultaneously or sequentially.

In some embodiments, the additional pharmaceutical agent is a JAK1 and/or JAK2 inhibitor. In some embodiments, the present application provides a method of treating a disease described herein (e.g., a B cell malignancy, such as diffuse B-cell lymphoma) in a patient comprising administering to the patient a compound described herein, or a pharmaceutically acceptable salt thereof, and a JAK1 and/or JAK2 inhibitor. The B cell malignancies can include those described herein and in U.S. Ser. No. 61/976,815, filed Apr. 8, 2014.

In some embodiments, the inhibitor of JAK1 and/or JAK2 is a compound of Table 1, or a pharmaceutically acceptable salt thereof. The compounds in Table 1 are selective JAK1 inhibitors (selective over JAK2, JAK3, and TYK2). The $IC_{50}$s obtained by the method of Assay A at 1 mM ATP are shown in Table 1.

TABLE 1

| # | Prep. | Name | Structure | JAK1 $IC_{50}$ (nM) | JAK2/JAK1 |
|---|---|---|---|---|---|
| 1 | US 2014/0121198, (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 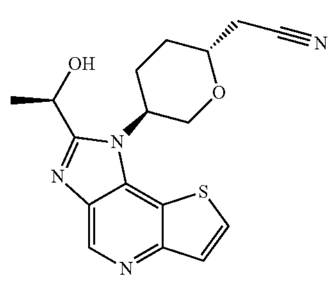 [SMILES: C[C@@H](O)c1nc2cnc3ccsc3c2n1[C@H]1CC[C@H](CC#N)OC1] | ++ | >10 |

TABLE 1-continued

| # | Prep. | Name | Structure | JAK1 IC$_{50}$ (nM) | JAK2/JAK1 |
|---|---|---|---|---|---|
| 2 | US 2014/0343030, (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 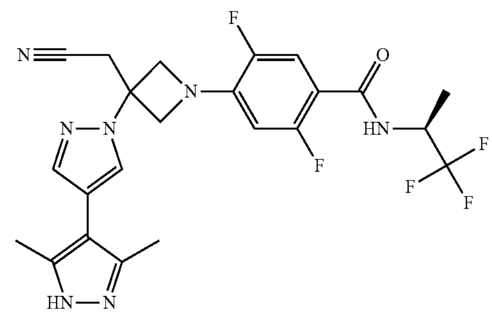 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 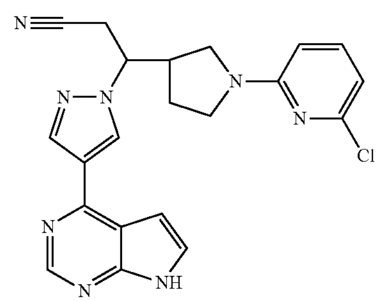 [SMILES: N#CCC(C1CCN(c2cccc(Cl)n2)C1)n1cc(-c2ncnc3[nH]ccc23)cn1] | + | >10 |
| 4 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 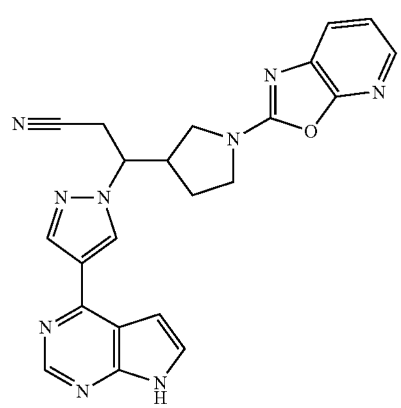 [SMILES: N#CCC(C1CCN(c2nc3cccnc3o2)C1)n1cc(-c2ncnc3[nH]ccc23)cn1] | + | >10 |
| 5 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 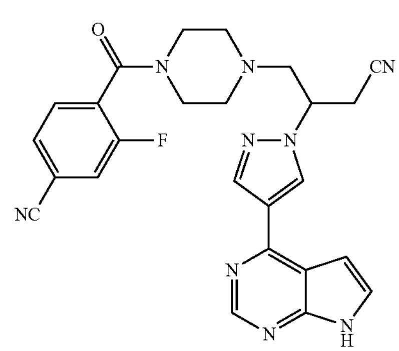 [SMILES: N#CCC(CN1CCN(C(=O)c2ccc(C#N)cc2F)CC1)n1cc(-c2ncnc3[nH]ccc23)cn1] | + | >10 |

TABLE 1-continued

| # | Prep. | Name | Structure | JAK1 IC$_{50}$ (nM) | JAK2/JAK1 |
|---|---|---|---|---|---|
| 6 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 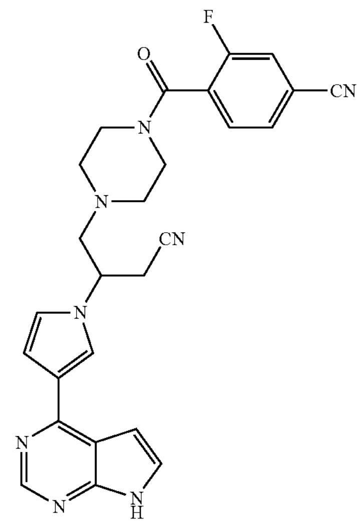 [SMILES: N#CCC(CN1CCN(C(=O)c2ccc(C#N)cc2F)CC1)n1ccc(-c2ncnc3[nH]ccc23)c1] | + | >10 |
| 7 | US 2011/0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 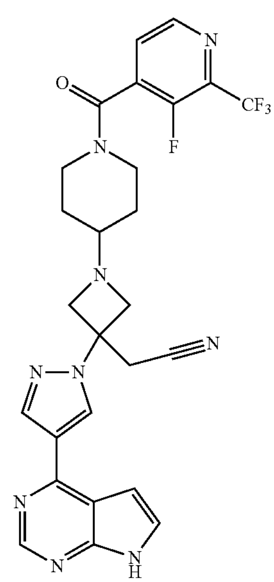 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE 1-continued

| # | Prep. | Name | Structure | JAK1 IC$_{50}$ (nM) | JAK2/JAK1 |
|---|---|---|---|---|---|
| 8 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 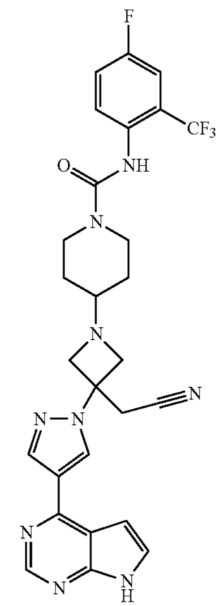 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | US 2011/0224190 (Example 85) | [3-[4-(7H-pyrrolo[2,3-d]pyrimidin-4-yl)-1H-pyrazol-1-yl]-1-(1-{[2,-(trifluoromethyl)pyrimidin-4-yl]carbonyl}piperidin-4-yl)azetidin-3-yl]acetonitrile | 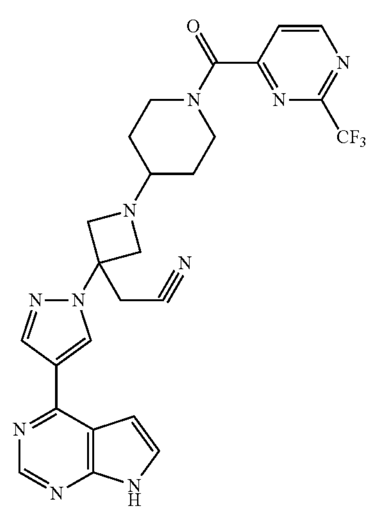 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE 1-continued

| # | Prep. | Name | Structure | JAK1 IC$_{50}$ (nM) | JAK2/ JAK1 |
|---|---|---|---|---|---|
| 10 | US 2012/ 0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 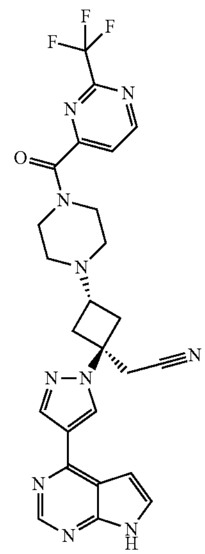 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/ 0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 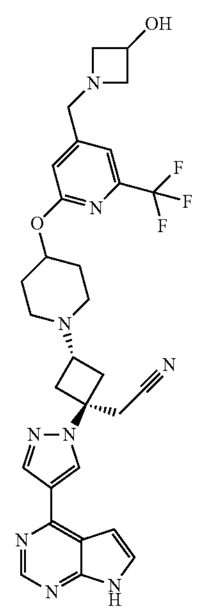 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| # | Prep. | Name | Structure | JAK1 IC$_{50}$ (nM) | JAK2/JAK1 |
|---|---|---|---|---|---|
| 12 | US 2012/0149681 (Example 161) | {trans-3-(4-{[4-{[2S]-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 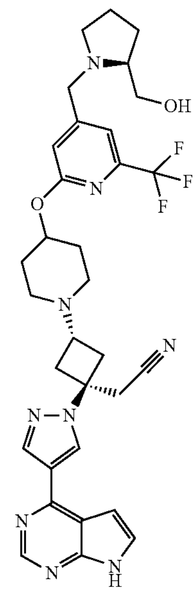 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 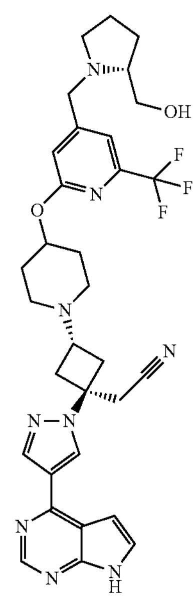 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 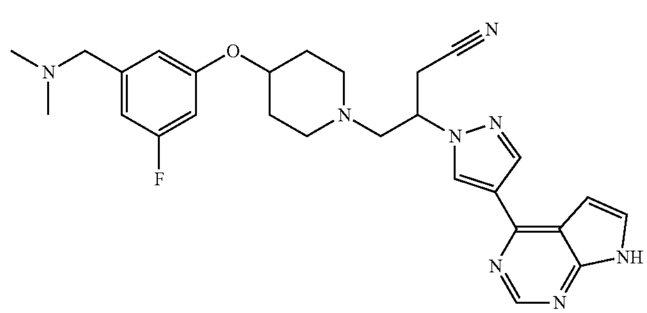 [SMILES: CN(C)Cc1cc(F)cc(OC2CCN(CC(CC#N)n3cc(-c4ncnc5[nH]ccc45)cn3)CC2)c1] | + | >10 |

TABLE 1-continued

| # | Prep. | Name | Structure | JAK1 IC$_{50}$ (nM) | JAK2/JAK1 |
|---|---|---|---|---|---|
| 15 | US 2013/0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 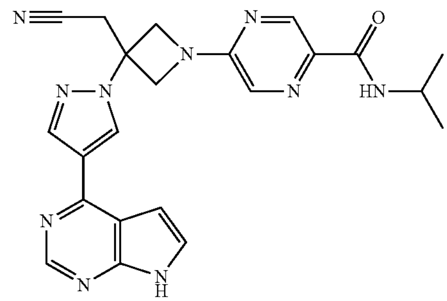 [SMILES: CC(C)NC(=O)c1cnc(N2CC(CC#N)(n3cc(-c4ncnc5[nH]ccc45)cn3)C2)cn1] | + | >10 |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 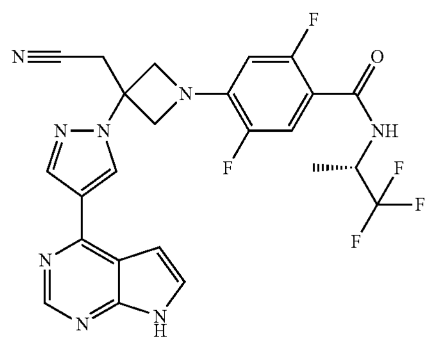 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 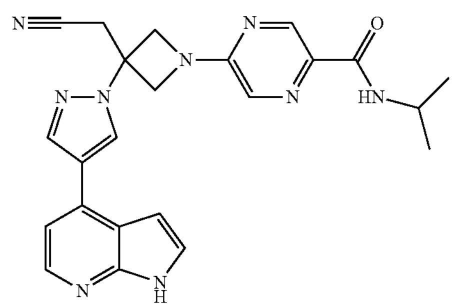 [SMILES: CC(C)NC(=O)c1cnc(N2CC(CC#N)(n3cc(-c4ccnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 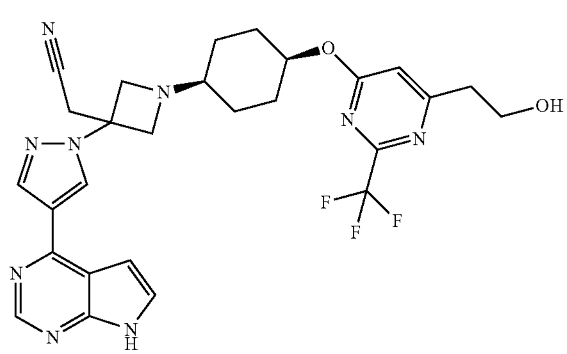 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE 1-continued

| # | Prep. | Name | Structure | JAK1 IC$_{50}$ (nM) | JAK2/ JAK1 |
|---|---|---|---|---|---|
| 19 | US 2013/ 0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 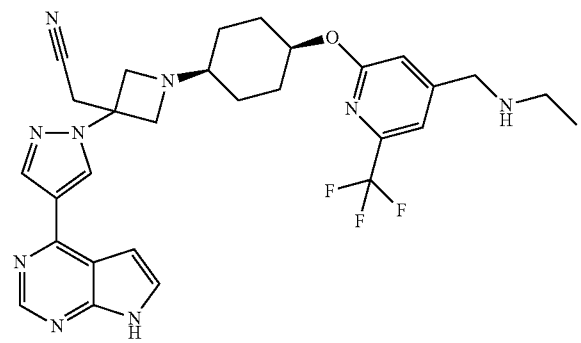 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/ 0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 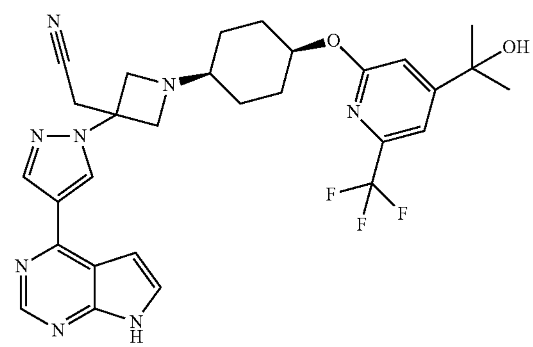 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 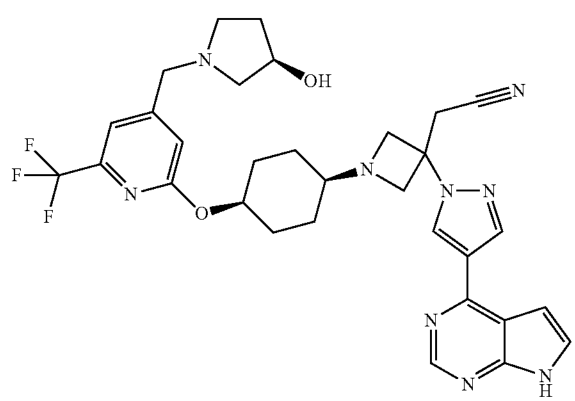 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 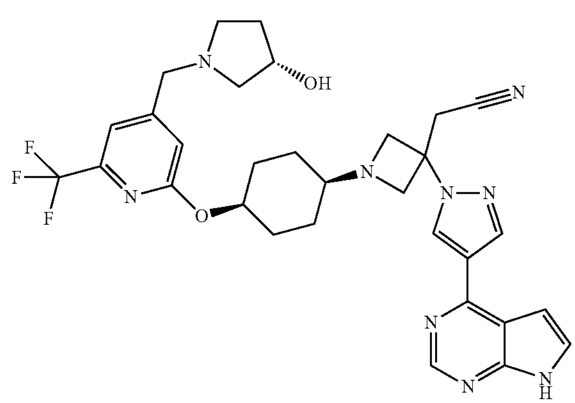 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE 1-continued

| # | Prep. | Name | Structure | JAK1 IC$_{50}$ (nM) | JAK2/JAK1 |
|---|---|---|---|---|---|
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 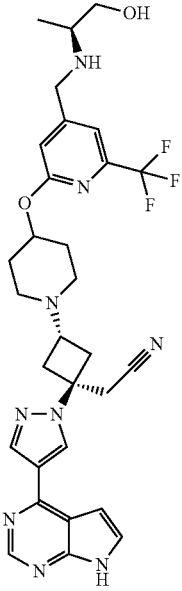 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 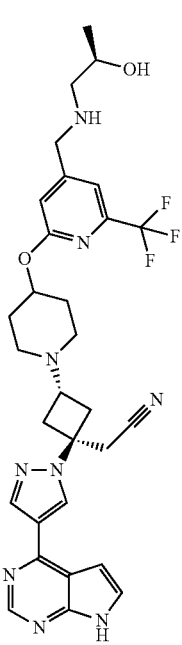 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| # | Prep. | Name | Structure | JAK1 IC$_{50}$ (nM) | JAK2/JAK1 |
|---|---|---|---|---|---|
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 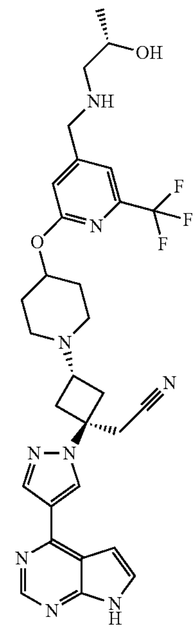 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 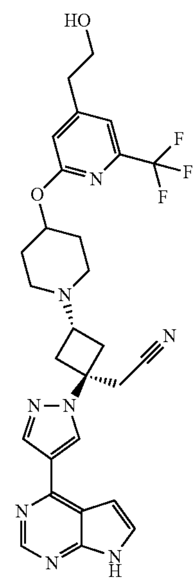 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM
++ means ≤100 nM
+++ means ≤300 nM
[a] Data for enantiomer 1
[b] Data for enantiomer 2

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the inhibitor of JAK1 and/or JAK2 is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the inhibitor of JAK1 and/or JAK2 is 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the inhibitor of JAK1 and/or JAK2 is selected from (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (R)-3-(1-[1,3]oxazolo[5,4-b]pyridin-2- ylpyrrolidin-3-yl)-3-[4-(7H-pyrrolo[2,3-d]pyrimidin-4-yl)-1H-pyrazol-1-yl]propanenitrile, (R)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or (R)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile, (S)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (S)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, (S)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile; and pharmaceutically acceptable salts of any of the aforementioned.

In some embodiments, the inhibitor of JAK1 and/or JAK2 is selected from the compounds of US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

Example antibodies for use in combination therapy include but are not limited to trastuzumab (e.g. anti-HER2), ranibizumab (e.g. anti-VEGF-A), bevacizumab (Avastin™, e.g. anti-VEGF), panitumumab (e.g. anti-EGFR), cetuximab (e.g. anti-EGFR), rituximab (Rituxan™, anti-CD20) and antibodies directed to c-MET.

One or more of the following agents may be used in combination with the salts or compounds of the present application and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101, 731, bendamustine (Treanda), ofatumumab, and GS-1101 (also known as CAL-101).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the salts and compounds of the invention can be used in combination with one or more other kinase inhibitors including imatinib, particularly for treating patients resistant to imatinib or other kinase inhibitors.

In some embodiments, the salts and compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present application with an additional agent. Furthermore, resistance of multiple myeloma cells to agents such as dexamethasone may be reversible upon treatment with the PI3K inhibitor of the present application. The agents can be combined with the present compound in a single or continuous dosage form, or the agents can be administered simultaneously or sequentially as separate dosage forms.

In some embodiments, a corticosteroid such as dexamethasone is administered to a patient in combination with the salts and compounds of the invention where the dexamethasone is administered intermittently as opposed to continuously.

In some further embodiments, combinations of the salts and compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds and salts of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound or salt of the invention (e.g., the hydrochloric acid salt of the compound Formula I), in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound or salt can be milled to provide the appropriate particle size prior to combining with the other ingredients. If the active compound or salt is substantially insoluble, it can be milled to a particle size of less than 200 mesh. If the active compound or salt is substantially water soluble, the particle size can be adjusted by milling to provide a substantially uniform distribution in the formulation, e.g. about 40 mesh.

The compounds and salts of the invention may be milled using known milling procedures such as wet milling to obtain a particle size appropriate for tablet formation and for other formulation types. Finely divided (nanoparticulate) preparations of the salts and compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain about 2.5, about 5, about 7.5, about 10, about 12.5, about 15, about 17.5, about 20, about 22.5, or about 25 mg of the active ingredient. In some embodiments, the compositions of the invention contain about 5 mg of the active ingredient. In some embodiments, the compositions of the invention contain about 10 mg of the active ingredient.

Similar dosages may be used of the compounds and salts described herein in the methods and uses of the invention.

The active compound or salt can be effective over a wide dosage range and is generally administered in a pharmaceutically effective amount. It will be understood, however, that the amount of the compound or salt actually administered will usually be determined by a physician, according to the relevant circumstances, including the condition to be treated, the chosen route of administration, the actual compound or salt administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound or salt of the present application. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present application.

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds, salts, and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound or salt of the invention. The topical formulations can be suitably packaged in tubes of, for example, 100 g which are optionally associated with instructions for the treatment of the select indication, e.g., psoriasis or other skin condition.

The amount of compound, salt, or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound or salt of the present application can vary according to, for example, the particular use for which the treatment is made, the manner of administration of the compound or salt, the health and condition of the patient, and the judgment of the prescribing physician. The proportion or concentration of a compound or salt of the invention in a pharmaceutical composition can vary depending upon a number of factors including dosage, chemical characteristics (e.g., hydrophobicity), and the route of administration. For example, the compounds and salts of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are provided herein.

Kits

The present application also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The hydrochloric acid salt of the compound of Formula I and the compound of Formula I have been found to be PI3K inhibitors according to at least one assay described herein.

EXAMPLES

The invention will be described in greater detail by way of specific examples. The following examples are offered for illustrative purposes, and are not intended to limit the invention in any manner. The example compounds, or salts thereof, containing one or more chiral centers were obtained in racemate form or as isomeric mixtures, unless otherwise specified.

General Methods

Preparatory LC-MS purifications of some of the compounds prepared were performed on Waters mass directed fractionation systems. The basic equipment setup, protocols, and control software for the operation of these systems have been described in detail in the literature. See e.g. "Two- Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm, 19×100 mm column, eluting with mobile phase A: 0.15% NH4OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Some of the compounds prepared were also analyzed via Differential Scanning Calorimetry (DSC). Typical DSC instrument conditions are as follows:

TA Instrument Differential Scanning Calorimetry, Model Q200 with autosampler: 30-350° C. at 10° C./min; T-zero aluminum sample pan and lid; nitrogen gas flow at 50 mL/min.

Mettler Toledo Differential Scanning calorimetry (DSC) 822 Instrument: 40-340° C. at a heating rate of 10° C./min.

Some of the compounds prepared were also analyzed via Thermogravimetric Analysis (TGA). Typical TGA instrument conditions are as follows:

TA Instrument Thermogravimetric Analyzer, Model Pyris: Temperature ramp from 25° C. to 300° C. at 10° C./min; nitrogen purge gas flow at 60 mL/min; TGA ceramic crucible sample holder.

TA Instrument Q500: Temperature ramp from 20° C. to 300° C. at 10° C./min.

Some of the compounds prepared were also analyzed via X-Ray Powder Diffraction (XRPD). Typical XRPD instrument conditions are as follows:

Bruker D2 PHASER X-Ray Powder Diffractometer instrument: X-ray radiation wavelength: 1.05406 Å CuKAI;

x-ray power: 30 KV, 10 mA; sample powder: dispersed on a zero-background sample holder; general measurement conditions: start Angle—5 degree, Stop Angle—60 degree, Sampling—0.015 degree, Scan speed—2 degree/min.

Rigaku Miniflex Powder Diffractometer: Cu at 1.054056 Å with Kβ filter; general measurement conditions: start Angle—3 degree, Stop Angle—45 degree, Sampling—0.02 degree, Scan speed—2 degree/min.

Example 1

Synthesis of (R)-4-(3-chloro-6-ethoxy-2-fluoro-5-((R)-1-hydroxyethyl)phenyl)pyrrolidin-2-one

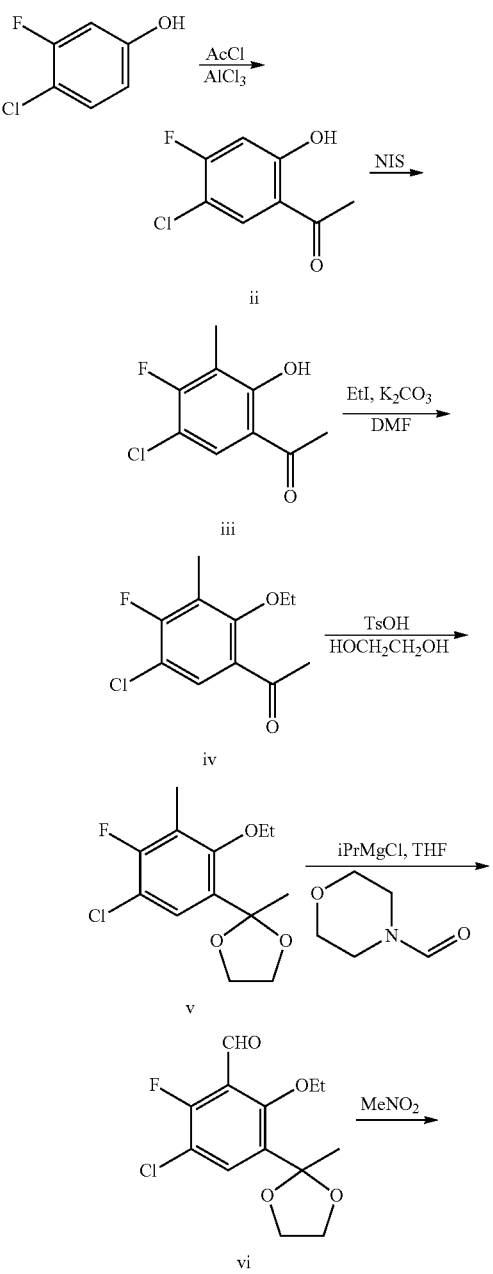

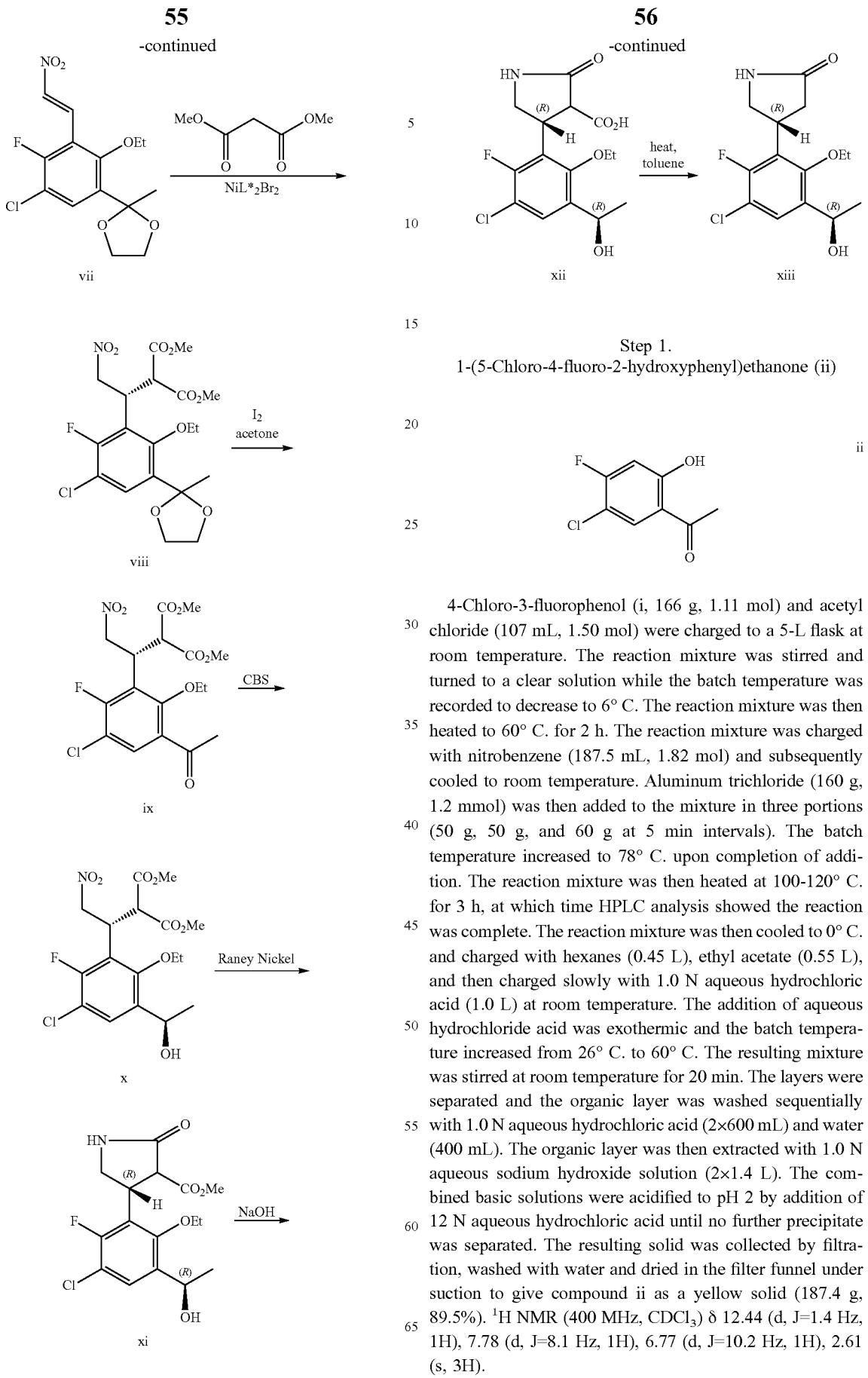

Step 1.
1-(5-Chloro-4-fluoro-2-hydroxyphenyl)ethanone (ii)

4-Chloro-3-fluorophenol (i, 166 g, 1.11 mol) and acetyl chloride (107 mL, 1.50 mol) were charged to a 5-L flask at room temperature. The reaction mixture was stirred and turned to a clear solution while the batch temperature was recorded to decrease to 6° C. The reaction mixture was then heated to 60° C. for 2 h. The reaction mixture was charged with nitrobenzene (187.5 mL, 1.82 mol) and subsequently cooled to room temperature. Aluminum trichloride (160 g, 1.2 mmol) was then added to the mixture in three portions (50 g, 50 g, and 60 g at 5 min intervals). The batch temperature increased to 78° C. upon completion of addition. The reaction mixture was then heated at 100-120° C. for 3 h, at which time HPLC analysis showed the reaction was complete. The reaction mixture was then cooled to 0° C. and charged with hexanes (0.45 L), ethyl acetate (0.55 L), and then charged slowly with 1.0 N aqueous hydrochloric acid (1.0 L) at room temperature. The addition of aqueous hydrochloride acid was exothermic and the batch temperature increased from 26° C. to 60° C. The resulting mixture was stirred at room temperature for 20 min. The layers were separated and the organic layer was washed sequentially with 1.0 N aqueous hydrochloric acid (2×600 mL) and water (400 mL). The organic layer was then extracted with 1.0 N aqueous sodium hydroxide solution (2×1.4 L). The combined basic solutions were acidified to pH 2 by addition of 12 N aqueous hydrochloric acid until no further precipitate was separated. The resulting solid was collected by filtration, washed with water and dried in the filter funnel under suction to give compound ii as a yellow solid (187.4 g, 89.5%). $^1$H NMR (400 MHz, CDCl$_3$) δ 12.44 (d, J=1.4 Hz, 1H), 7.78 (d, J=8.1 Hz, 1H), 6.77 (d, J=10.2 Hz, 1H), 2.61 (s, 3H).

Step 2. 1-(5-Chloro-4-fluoro-2-hydroxy-3-iodophenyl)ethanone (iii)

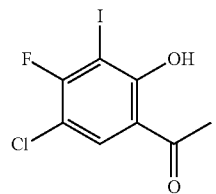

iii 1-(5-Chloro-4-fluoro-2-hydroxyphenyl)ethanone (ii, 100.0 g, 530.3 mmol) was dissolved in acetic acid (302 mL) and N-iodosuccinimide (179.2 g, 796.5 mmol) was added to the solution. The reaction mixture was stirred at from about 61° C. to about 71° C. for 2 h, at which time HPLC analysis indicated that the reaction was complete. The reaction mixture was then cooled to room temperature, water (613 mL) was added, and the resulting slurry was stirred at room temperature for 30 min. The product was collected by filtration and rinsed with water to afford brown solids. The wet product was dissolved in acetic acid (400 mL) at 60° C. Water (800 mL) was added (over 15 min) to the solution to precipitate pure product. The product was collected by filtration and washed with water (100 mL). The product was dried on the filter funnel under suction for 18 h to give compound iii as a brown solid (164.8 g, 95.0% yield). $^1$H NMR (300 MHz, DMSO-d$_6$) δ13.34 (s, 1H), 8.26 (d, J=8.4 Hz, 1H), 2.68 (s, 3H).

Step 3. 1-(5-Chloro-2-ethoxy-4-fluoro-3-iodophenyl)ethanone (iv)

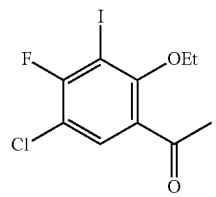

iv

In a 5-L three-necked round bottom flask equipped with a condenser and a thermometer, 1-(5-chloro-4-fluoro-2-hydroxy-3-iodophenyl)ethanone (iii, 280 g, 840 mmol) was dissolved in N,N-dimethylformamide (600 mL). During the dissolution, the internal temperature dropped from 19.3° C. to 17.0° C. Iodoethane (81.2 mL, 1020 mmol) was added to the resulting mixture. Potassium carbonate (234 g, 1690 mmol) was then added over 2 min to the reaction mixture and no change in the batch temperature was observed. The reaction mixture was heated to 60° C. for 3 h, at which time HPLC analysis indicated the reaction was complete. The reaction mixture was allowed to cool to room temperature and the product was collected by filtration. The solids were dissolved in a mixture of DCM (1.0 L), hexane (500 ml), and water (2.1 L). The biphasic system was stirred at 20° C. for 20 min. The layers were separated and the aqueous layer was extracted with DCM (1.0 L). The combined organic layer was washed with water (2×250 mL) and brine (60 mL). The organic phase was separated, dried over anhydrous Na$_2$SO$_4$, filtered, and concentrated in vacuo to dryness to give compound iv as a yellow solid (292 g, 94% yield). $^1$H NMR (400 MHz, DMSO-d$_6$) δ7.69 (d, J=8.4 Hz, 1H), 3.95 (q, J=7.0 Hz, 2H), 2.62 (s, 3H), 1.49 (t, J=7.0 Hz, 3H). LCMS for C$_{10}$H$_{10}$ClFIO$_2$ (M+H)$^+$: m/z=342.9.

Step 4. 2-(5-chloro-2-ethoxy-4-fluoro-3-iodophenyl)-2-methyl-1,3-dioxolane (v)

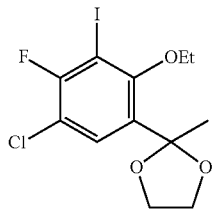

v

A solution of 1-(5-chloro-2-ethoxy-4-fluoro-3-iodophenyl)ethanone (iv, 250.0 g, 693.4 mmol) and 1,2-ethanediol (58.0 mL, 1040 mmol) in toluene (1.5 L) was treated with p-toluenesulfonic acid monohydrate (10.6 g, 55.5 mmol). The reaction flask was fitted with a Dean-Stark trap and the mixture was heated at reflux for 7 h. LCMS analysis indicated that the reaction mixture contained 8.3% starting material and 91.7% product. The reaction mixture was cooled to 106° C., and additional amount of 1,2-ethanediol (11.6 mL, 208 mmol) was introduced via syringe. The reaction mixture was then heated at reflux for an additional 8 h. LCMS analysis indicated that the reaction mixture contained 3.6% starting material and 96.4% product. The reaction mixture was cooled to 106° C., and additional 1,2-ethanediol (7.73 mL, 139 mmol) was introduced via syringe. The reaction mixture was heated under reflux for additional 15.5 h. LCMS analysis indicated that the reaction mixture contained 2.2% starting material and 97.8% product.

The reaction mixture was then cooled to 0° C. and water (200 ml) and aqueous saturated NaHCO$_3$ (300 ml) were added to adjust the mixture to a pH of 9. DCM (200 ml) was added and the batch was stirred for 10 min. The layers were separated and the aqueous layer was extracted with toluene (300 mL). The combined organic layer was washed sequentially with a mixture of water (200 ml) and aqueous saturated NaHCO$_3$ (200 ml), water (300 ml), brine (300 ml), dried over anhydrous Na$_2$SO$_4$, filtered, and concentrated in vacuo to dryness to provide the crude compound v as light brown solid (268 g 100% yield). $^1$H NMR (400 MHz, CDCl$_3$) δ 7.59 (d, J=8.6 Hz, 1H), 4.26-3.96 (m, 4H), 3.92-3.72 (m, 2H), 1.74 (s, 3H), 1.50 (t, J=7.0 Hz, 3 H). LCMS for C$_{12}$H$_{14}$CFIO$_3$ (M+H)$^+$: m/z=387.0.

Step 5. 3-chloro-6-ethoxy-2-fluoro-5-(2-methyl-1,3-dioxolan-2-yl)benzaldehyde (vi)

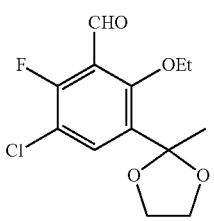

vi

To a stirred solution of 2-(5-chloro-2-ethoxy-4-fluoro-3-iodophenyl)-2-methyl-1,3-dioxolane (v, 135.0 g, 349.2 mmol) (86.8% purity by HPLC with 5.5% of the ketone) in anhydrous tetrahydrofuran (300 mL) at about 0° C. to about 3° C. was slowly added 1.3 M isopropylmagnesium chloride lithium chloride complex in THF (322.3 mL, 419.0 mmol) over 1 h. The reaction mixture was stirred at from about 0°

C. to about 5° C. for 30 min. at which time LCMS analysis indicated the iodo-magnesium exchange reaction was complete. N-Formylmorpholine (71.1 mL, 700 mmol) was then added to the reaction mixture over 1 h at from about 0° C. to about 8° C. The reaction mixture was stirred at from about 0° C. to about 8° C. for an additional 1 h, at which time LCMS and HPLC analyses showed the starting material was consumed and a significant amount of de-iodination byproduct, 2-(5-chloro-2-ethoxy-4-fluorophenyl)-2-methyl-1,3-dioxolane was observed. The reaction was quenched with an aqueous solution of citric acid (120.8 g, 628.6 mmol) in water (1.20 L) at 0° C. The quenched reaction mixture was then extracted with EtOAc (2×600 mL). The phases were readily separated. The combined organic layer was washed sequentially with water (300 ml) and brine (500 mL), dried over anhydrous $Na_2SO_4$, filtered, and concentrated in vacuo. The residue was purified by flash column chromatography on silica gel with 0-10% EtOAc/hexane to give the crude product compound vi as a pale yellow solid, which was a mixture of the desired product, 3-chloro-6-ethoxy-2-fluoro-5-(2-methyl-1,3-dioxolan-2-yl)benzaldehyde(vi, 80 g, 80%) containing 36 mol % of the de-iodination by-product, 2-(5-chloro-2-ethoxy-4-fluorophenyl)-2-methyl-1,3-dioxolane as indicated by NMR analysis. The crude product compound vi was further purified by formation of the corresponding sodium bisulfite adduct.

Sodium bisulfite (36.91 g, 354.7 mmol) was dissolved in water (74.3 mL, 4121 mmol). To a stirred solution of crude 3-chloro-6-ethoxy-2-fluoro-5-(2-methyl-1,3-dioxolan-2-yl) benzaldehyde (vi, 80.00 g, 177.3 mmol) in ethyl acetate (256.0 mL), the freshly prepared sodium bisulfite solution was added in one portion. The solution was stirred for about 10 min and precipitates were observed. The slurry was then stirred for an additional 1 h. The aldehyde-bisulfite adduct was collected by filtration, washed with EtOAc and dried under vacuum and nitrogen atmosphere for 20 h to give a white solid (58.2 g, 83.6% yield). To the aldehyde-bisulfite adduct (58.2 g, 148 mmol) mixed in 1.0 M aqueous sodium hydroxide (296 mL, 296 mmol) was added methyl t-butyl ether (600 mL) (MTBE). The reaction mixture was stirred at room temperature for 6 min to give a clear biphasic mixture, and stirring was continued for an additional 5 min. The organic phase was collected and the aqueous layer was extracted with MTBE (2×300 mL). The combined organic layers were washed with brine (300 mL), dried over anhydrous $Na_2SO_4$, filtered, and concentrated in vacuo to give pure compound vi as a white crystalline solid (31.4 g, 73.4% yield). $^1$H NMR (400 MHz, $CDCl_3$) δ 10.27 (s, 1H), 7.78 (d, J=8.5 Hz, 1H), 4.10-3.96 (m, 4H), 3.87-3.76 (m, 2H), 1.72 (s, 3H), 1.44 (t, J=7.0 Hz, 3 H). LCMS for $C_{13}H_{15}ClFO_4$ (M+H)$^+$: m/z=289.0.

Step 6. (E)-2-(5-chloro-2-ethoxy-4-fluoro-3-(2-nitrovinyl)phenyl)-2-methyl-1,3-dioxolane (vii)

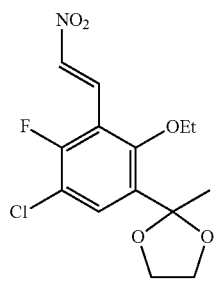

vii

Into a 5-L 4-neck round bottom flask equipped with overhead stirrer, septa, thermocouple, nitrogen inlet and condenser was charged 3-chloro-6-ethoxy-2-fluoro-5-(2-methyl-1,3-dioxolan-2-yl)benzaldehyde (vi, 566.2 g, 1961 mmol), nitromethane (1060 mL, 19600 mmol), and glacial acetic acid (1120 mL). Next, the reaction mixture was charged with benzylamine (53.6 mL, 490 mmol) and the resulting mixture was heated to 60° C. and the reaction was monitored by LCMS for 5.5 h. An initial baseline analysis was taken at t=0. The reaction was checked after 2 h and 5 h. After 2 h, there was about 20% of starting material aldehyde unreacted. After 5 h the reaction profile was as follows: starting material compound vi (<2%), intermediate imine (<4%), product compound vii (>93%) and benzylamine Michael adduct (not detected). At the reaction time of 5.5 h, the reaction was deemed complete. The reaction mixture was cooled to room temperature and diluted with ethyl acetate (3.0 L). The mixture was split in half for workup due to the large volume involved.

Each half was treated according to the following procedure: The reaction mixture was first washed with 1.5 M NaCl in water (2×1500 mL; after each wash the aqueous volume output increased compared to input suggesting that acetic acid and/or nitromethane were being removed). The mixture was then cooled to about 15° C. and washed with 4 M aqueous NaOH solution (4×300 mL) until the aqueous extract reached pH of 8-9. During initial washes the aqueous layer remained acidic, but as the aqueous became slightly basic during subsequent washes the mixture heated up and the extract was dark. The layers were separated. The organic layer after the pH adjustment was then washed with 1.5 M sodium chloride in water (1000 mL) and water (500 mL). Emulsion and slow partition were observed during these final washes. The organic phase was dried over anhydrous $MgSO_4$, filtered, and concentrated under reduced pressure. The resulting amber syrup was placed under high vacuum overnight. The syrup solidified and 740 g of crude product was obtained.

Heptane (1.3 L) was added to the crude product, forming a slurry, which was heated in a 60° C. water bath until all the solids were dissolved. The resulting solution was polish filtered into a clean 3-L 4-neck round bottom flask equipped with an overhead stirrer and nitrogen inlet. The filter was rinsed with heptane (40 mL). The filtered solution was cooled to room temperature and stirred for 5 h. Solid precipitates were observed and the slurry was cooled to 0° C. in an ice bath for 1 h. Product was collected by filtration and the resulting wet cake was washed with 500 mL of ice cold heptane. The product was partially dried on the filter under vacuum suction and further dried under high vacuum overnight. The filtrate and wash solution were concentrated under reduced pressure and the resulting residue was held for column purification.

Solids from heptane crystallization were dissolved in a small volume of DCM and 20% EtOAc/hexane and loaded onto a column containing about 1 kg of silica gel. The column was eluted with 20% EtOAc/hexane. The desired fractions were combined and concentrated under reduced pressure to give a yellow solid. The solid was dried under high vacuum overnight to give 497 g of product compound vii as a pale yellow crystalline solid.

The concentrated filtrate and wash from the heptane crystallization was loaded onto the same column as above using 20% EtOAc/hexane. The column was eluted using the same solvent system as above to remove baseline impurities and residual acetic acid. The desired fractions were combined and concentrated under reduced pressure to give a reddish amber oil. The oil was placed under high vacuum and about 220 g of crude product was obtained. This crude product was dissolved in heptane (500 mL) and seeded with a small amount of the first crop solid product. The slurry was stirred at room temperature for 16 h and then cooled in an ice bath for 3 h. The second crop product was collected by filtration. The product was dried under high vacuum and 110 g of product was obtained as yellow solid. The total amount of product compound vii obtained was 607 g (93.3% yield). $^1$H NMR (400 MHz, DMSO-$d_6$) δ 7.94 (s, 2H), 7.68 (d, J=8.9 Hz, 1H), 4.07-3.95 (m, 4H), 3.82-3.73 (m, 2H), 1.65 (s, 3H), 1.39 (t, J=7.0 Hz, 3H). LCMS for $C_{14}H_{16}ClFNO_5$ (M+H)$^+$: m/z=332.0.

Step 7. (R)-Dimethyl-2-(1-(3-chloro-6-ethoxy-2-fluoro-5-(2-methyl-1,3-dioxolan-2-yl)phenyl)-2-nitroethyl)malonate (viii)

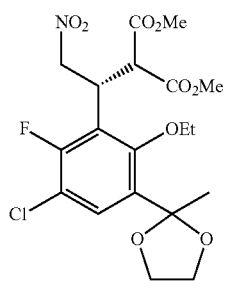

Into a 2-L round bottom flask with a magnetic stir bar and nitrogen inlet containing (E)-2-(5-chloro-2-ethoxy-4-fluoro-3-(2-nitrovinyl)phenyl)-2-methyl-1,3-dioxolane (vii, 352.8 g, 1064 mmol) was added anhydrous tetrahydrofuran (1.06 L) and dimethyl malonate (146 mL, 1280 mmol). (1S,2S)-N,N'-dibenzylcyclohexane-1,2-diamine-dibromonickel (Evans' Catalyst, 21.4 g, 26.6 mmol), was charged to the reaction mixture. The reaction mixture was brown in color and a homogeneous solution was observed. The reaction mixture was stirred at room temperature for 18.5 h. The reaction was analyzed after 18.5 h by HPLC. Unreacted starting material, compound vii, was present at 2%. The reaction mixture was concentrated under reduced pressure to remove THF and the resulting residue was purified by flash chromatography (DCM/hexanes used for loading, 1422 g of silica gel was used for this column, and the column was eluted with 10% to 20% EtOAc/hexane; column fractions were monitored by TLC using 30% EtOAc/hexane as eluent and was visualized by UV). The desired fractions were combined and concentrated under reduced pressure. The residue was dried under high vacuum. Over time, the syrup solidified to light yellow solids (503.3 g) and a sample was taken for chiral HPLC analysis. Chiral purity was 95.7% of the desired (R)-enantiomer and 4.3% of the undesired (S)-enantiomer. Ethanol (1.0 L) was added to the solids and the mixture was heated in a 60° C. water bath until the solids were dissolved. The solution was polish filtered into a clean 3-L 4-neck round bottom through #1 Whatman filter paper. The filtered solution was cooled to room temperature while stirring. Crystallization was observed after 30 min of stirring and the slurry was stirred at room temperature for 16 h. The slurry was cooled in an ice bath for 1 h. The product was collected by filtration and the resulting filter cake was washed with ice cold ethanol (500 mL) and was partially dried on the filter. The solids were dried under high vacuum to give the desired product viii (377.5 g) as white crystalline solids. The chiral purity was determined by chiral HPLC to be 100% of the desired (R)-enantiomer and 0% of the undesired (S)-enantiomer.

The filtrate and wash were combined and concentrated under reduced pressure to an oil (118.9 g). The oil was dissolved in ethanol (475.0 mL) (4 mL/g) and was seeded with the first crop crystals. The resultant slurry was stirred for 16 h at room temperature and then cooled in an ice bath for 5.5 h. The second crop product was isolated by filtration and was partially dried on the filter. It was dried under high vacuum to give the second crop product (31.0 g). The chiral purity was determined by chiral HPLC to be 98.3% of the desired (R)-enantiomer and 1.7% of the undesired (S)-enantiomer. The combined yield of the first and second crops of product was 408.5 g in 82.8% yield. $^1$H NMR (500 MHz, DMSO-$d_6$) δ 7.51 (d, J=9.0 Hz, 1H), 5.20-4.81 (m, 2H), 4.62 (m, 1H), 4.14-4.03 (m, 2H), 4.03-3.97 (m, 2H), 3.95-3.88 (m, 1H), 3.84-3.72 (m, 2H), 3.70 (s, 3H), 3.38 (s, 3H), 1.61 (s, 3H), 1.39 (t, J=6.9 Hz, 3H). LCMS for $C_{19}H_{24}ClFO_9$ (M+H)$^+$: m/z=463.9.

Step 8. (R)-Dimethyl 2-(1-(3-acetyl-5-chloro-2-ethoxy-6-fluorophenyl)-2-nitroethyl)malonate (ix)

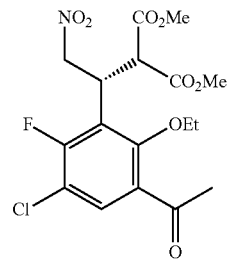

To a stirred solution of (R)-dimethyl-2-(1-(3-chloro-6-ethoxy-2-fluoro-5-(2-methyl-1,3-dioxolan-2-yl)phenyl)-2-nitroethyl)malonate (viii, 244.0 g, 526.0 mmol) in acetone (1.2 L) in a three-necked 5-L round bottom flask, equipped with a mechanical stirrer, was added iodine (13.4 g, 52.6 mmol) at room temperature. The resulting brown solution was heated at 50° C. in a water bath for 30 min, at which time LCMS analysis showed the reaction was complete. The reaction mixture was cooled to room temperature, and then quenched with a solution of sodium thiosulfate (17.0 g, 108 mmol) in water (160 mL) to give a pale yellow clear solution. At this time, an additional amount of water (1.2 L) was charged to the quenched solution and the resulting white slurry was stirred at room temperature for 1 h. The solid was then collected by filtration and re-dissolved in acetone (1.4 L) at 40° C. The solution was cooled to room temperature, and then additional water (1.4 L) was added. The resulting white slurry was stirred at room temperature for 1 h. The solid was collected by filtration and washed with water (3×100 ml). The solid product was dried in a filter funnel under suction with a nitrogen flow for 46 h to give compound ix as a white solid (212 g, 96% yield). $^1$H NMR (300 MHz, CDCl$_3$) δ 7.54 (d, J=8.6 Hz, 1H), 5.09-4.67 (m, 3H), 4.10-3.83 (m, 3H), 3.90 (s, 3H), 3.57 (s, 3H), 2.57 (s, 3H), 1.46 (t, J=7.0 Hz, 3H). LCMS for $C_{17}H_{20}ClFNO_8$ (M+H)$^+$: m/z=420.1.

Step 9. Dimethyl 2-((R)-1-(3-chloro-6-ethoxy-2-fluoro-5-((R)-1-hydroxyethyl)phenyl)-2-nitroethyl)malonate (x)

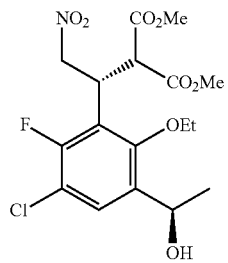

To a stirred solution of (3aS)-1-methyl-3,3-diphenyltetrahydro-3H-pyrrolo[1,2-c][1,3,2]oxazaborole, ((S)-MeCBS, 16.39 g, 59.12 mmol, 0.1 eq.) in anhydrous THF (100 mL) in a 5 L round bottom flask at room temperature were added a solution of 1.0 M borane-THF complex in THF (591 mL, 591 mmol, 1 eq.) followed by boron trifluoride etherate (3.75 mL, 29.6 mmol, 0.05 eq). The resulting solution was stirred at room temperature for 30 min. A solution of dimethyl [(1R)-1-(3-acetyl-5-chloro-2-ethoxy-6-fluorophenyl)-2-nitroethyl]malonate (ix, 253.0 g, 591.2 mmol) in anhydrous THF (1.7 L) was then added dropwise via an addition funnel over 60 min. The flask that contained the ketone ix was rinsed with anhydrous THF (135 mL) and the solution was added dropwise via the addition funnel to the reaction mixture. The resulting solution was stirred at room temperature for an additional 10 min, at which time LCMS analysis showed complete conversion of the ketone to the alcohol. The reaction was quenched by dropwise addition of methanol (71.8 mL, 1770 mmol) at 0° C. The quenched reaction mixture was stirred at room temperature for 15 min before it was concentrated in vacuo to give the crude product. The crude products of this batch and a similar batch (using 200 g of starting material) were combined and was purified by silica gel column chromatography using 0 to 5% of MeOH/DCM as eluent to give compound x as a white solid (437 g, 97.9% yield). $^1$H NMR (300 MHz, CDCl$_3$) δ 7.50 (d, J=8.8 Hz, 1H), 5.13 (q, J=6.3 Hz, 1H), 5.01-4.65 (m, 3H), 4.14-3.89 (m, 3H), 3.79 (s, 3H), 3.57 (s, 3H), 1.57-1.42 (m, 6H). LCMS for C$_{17}$H$_{21}$ClFNNaO$_8$ (M+Na): m/z=444.0.

Step 10. (4R)-Methyl 4-(3-chloro-6-ethoxy-2-fluoro-5-((R)-1-hydroxyethyl)phenyl)-2-oxopyrrolidine-3-carboxylate (xi)

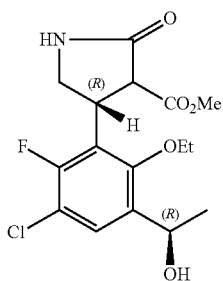

A 3-necked Morton round bottom flask containing dimethyl ((1R)-1-{3-chloro-6-ethoxy-2-fluoro-5-[(1R)-1-hydroxyethyl]phenyl}-2-nitroethyl)malonate (x, 100.0 g, 237.1 mmol) in tetrahydrofuran (800.0 mL) and Raney Nickel (120 g after removal of water by a pipette) was fitted with a condenser, a mechanical stirrer (glass stirring rod and Teflon bearing), and two hydrogen gas balloons (after vacuum purging). The flask was placed in an oil bath at 65° C. The batch was stirred vigorously for 16 h and the balloons were periodically removed and refilled with hydrogen. A sample was taken and analyzed by HPLC. The product, compound xi, was present at 83%. There were 7.8% of uncyclized amine and 5.5% of hydroxylamine side-product in the reaction mixture. Catalyst was filtered off (care must be taken not to allow Raney nickel to go dry to expose to air). The filtrate was evaporated to dryness to give 91 g of crude product as a white foam. The crude product (91 g, 82.6% area purity) was combined with another similar batch of crude product (93 g, 72.8% purity) for purification. The combined crude product (184 g) was purified by column chromatography on silica gel (EtOAc/hexane as eluent) to give compound xi (101.1 g, 93% HPLC purity, 59.3% crude yield). The crude material was used for the next step without further purification. LCMS for C$_{16}$H$_{20}$ClFNO$_5$ (M+H)$^+$: m/z=360.0.

Step 11. (4R)-4-(3-chloro-6-ethoxy-2-fluoro-5-((R)-1-hydroxyethyl)phenyl)-2-oxopyrrolidine-3-carboxylic acid (xii)

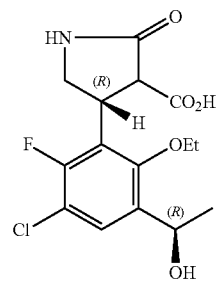

Into a 5 L, 4-neck round bottom flask equipped with an overhead stirrer and a nitrogen inlet was charged a solution of (4R)-methyl 4-(3-chloro-6-ethoxy-2-fluoro-5-((R)-1-hydroxyethyl)phenyl)-2-oxopyrrolidine-3-carboxylate (xi, 268 g, 581 mmol) in tetrahydrofuran (2150 mL, 26500 mmol). To the solution, 1.0 M sodium hydroxide in water (1420 mL, 1420 mmol) was charged. The resulting cloudy solution became clear within 1 min. The reaction mixture was stirred overnight at room temperature. The reaction was analyzed by LCMS after 15 h and appeared to be complete as the starting material was not observed. The reaction mixture was cooled in an ice bath to an internal temperature of 9.5° C. and the mixture was acidified to pH 1-2 by addition of 6.0 M aqueous hydrochloric acid (237.0 mL, 1422 mmol) via a dropping funnel over 30 min. The reaction mixture was divided in half and each half was extracted with ethyl acetate (2×1 L). The combined aqueous layers were further extracted with ethyl acetate (500 mL).

The two organic layers were washed with brine (20% w/w NaCl/water, 2×1000 mL), dried over anhydrous MgSO$_4$, filtered, and concentrated to give the crude intermediate acid xii as a yellowish foam which was used directly in the next reaction. $^1$H NMR (400 MHz, DMSO-d$_6$) δ12.68 (br s, 1H), 8.26 (s, 1H), 7.52 (d, J=8.0 Hz, 1H), 5.27 (br s, 1H), 4.90 (q, J=6.3 Hz, 1H), 4.28 (q, J=8.8 Hz, 1H), 3.92-3.81 (m, 1H), 3.76-3.65 (m, 1H), 3.57 (t, J=9.6 Hz, 1H), 3.46 (d, J=9.4 Hz, 1H), 3.23 (q, J=9.5 Hz, 1H), 1.33 (t, J=6.9 Hz, 3H), 1.28 (d, J=6.4 Hz, 3H). LCMS for C$_{15}$H$_{17}$ClFNNaO$_5$ (M+Na): m/z=368.0.

Step 12. (R)-4-(3-chloro-6-ethoxy-2-fluoro-5-((R)-1-hydroxyethyl)phenyl)pyrrolidin-2-one (xiii)

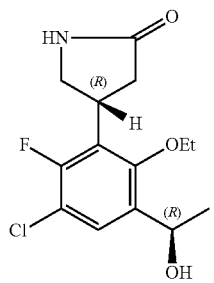

xiii

The crude compound xii was dissolved in 1,4-dioxane (976 mL) and toluene (976 mL) and the resulting yellow solution was heated at 100° C. The color of the solution became brown as the reaction progressed. Samples were drawn at 1 h, 2 h and 2.5 h time points. At 2.5 h, HPLC analysis showed the acid, compound 12, was at 0.38% and the desired product, compound xiii, at 78.8%. The reaction mixture was cooled to room temperature and was polished filtered into a clean 3-L round-bottom flask. The solution was then concentrated under reduced pressure and the resulting residue was placed under high vacuum to give a brown foam (254 g).

Acetonitrile (350 mL) was charged to the brown syrup and heated in a 65° C. water bath until dissolution was observed. The solution was cooled to room temperature and was stirred for 16 h. Solids were separated out of solution. The resulting slurry was cooled in an ice bath for 1 h. The product was collected by filtration and the filter cake was rinsed with 400 mL of ice cold acetonitrile. The solids appeared to be hygroscopic. The solid was dissolved in DCM (2.0 L) and concentrated to a syrup which was placed under high vacuum to yield compound xiii as a white foam (106.4 g).

The filtrate was concentrated to a dark syrup (about 120 g) which was purified by flash chromatography (4×330 g silica gel columns, loaded with DCM, eluted with 50% to 100% EtOAc/hexane, and monitored by TLC using 100% EtOAc as eluent). Fractions from chromatography were concentrated under reduced pressure and placed under high vacuum to yield a light brown foam (54.4 g). The foam was charged with MTBE (400 mL) and MeOH (10 mL) and heated in a 56° C. water bath for 15 minutes and some solids remained. The slurry was cooled to room temperature with stirring. The slurry was filtered to remove insoluble substances. The filtrate was concentrated to a syrup and placed under high vacuum to yield a foam. The foam was charged with acetonitrile (72 mL, 1.5 mL/g) and heated in a 60° C. water bath until the solution becomes homogeneous. The solution was cooled to room temperature with stirring and solids precipitated out of solution and became very thick. Additional acetonitrile (24 mL) was charged to adjust the dilution to 2 mL/g. The slurry was stirred at room temperature for 16 h and then cooled in an ice bath for 1 hour. The product was collected by filtration and rinsed with acetonitrile. Compound xiii (25 g) was obtained as second crop. A total of 131.4 g of compound xiii was obtained in 74.9% yield from compound xi. $^1$H NMR (400 MHz, DMSO-$d_6$) δ 7.83 (s, 1H), 7.47 (d, J=8.7 Hz, 1H), 5.24 (d, J=4.5 Hz, 1H), 4.96-4.85 (m, 1H), 4.08-3.92 (m, 1H), 3.80 (qt, J=6.9, 3.5 Hz, 2H), 3.61-3.51 (m, 1H), 3.25 (t, J=9.1 Hz, 1H), 2.61-2.50 (m, 1H), 2.35-2.26 (m, 1H), 1.33 (t, J=7.0 Hz, 3H), 1.27 (d, J=6.4 Hz, 3H). LCMS for $C_{14}H_{18}ClFNO_3$ (M+H)$^+$: m/z=302.0.

Example 2

Alternative Synthesis of (R)-4-(3-chloro-6-ethoxy-2-fluoro-5-((R)-1-hydroxyethyl)phenyl)pyrrolidin-2-one

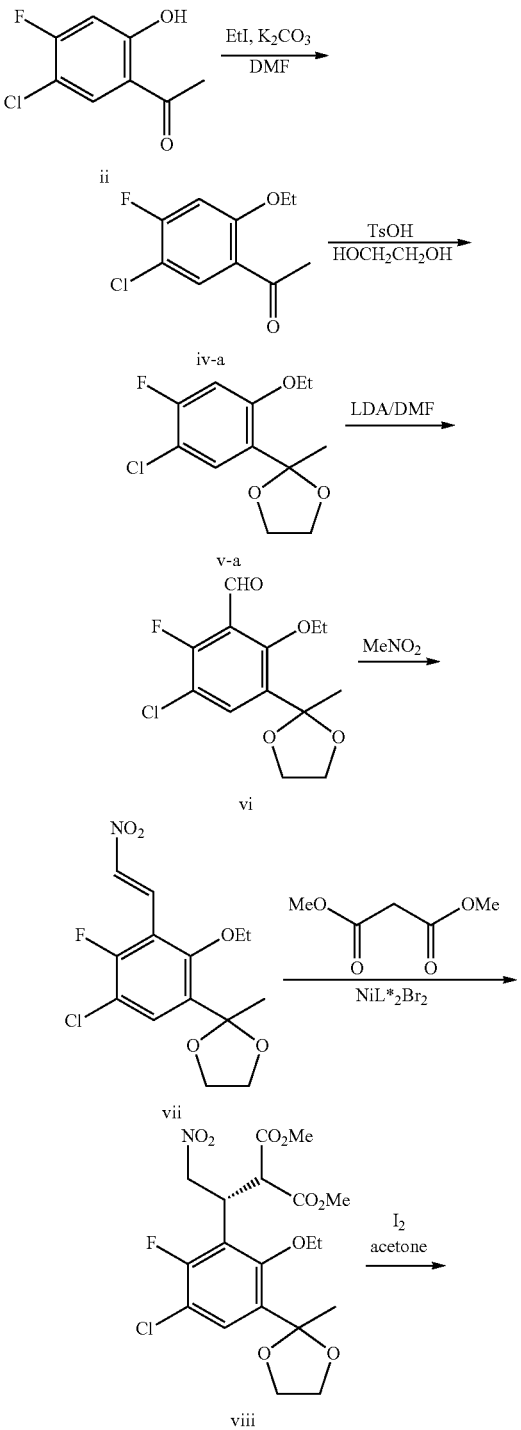

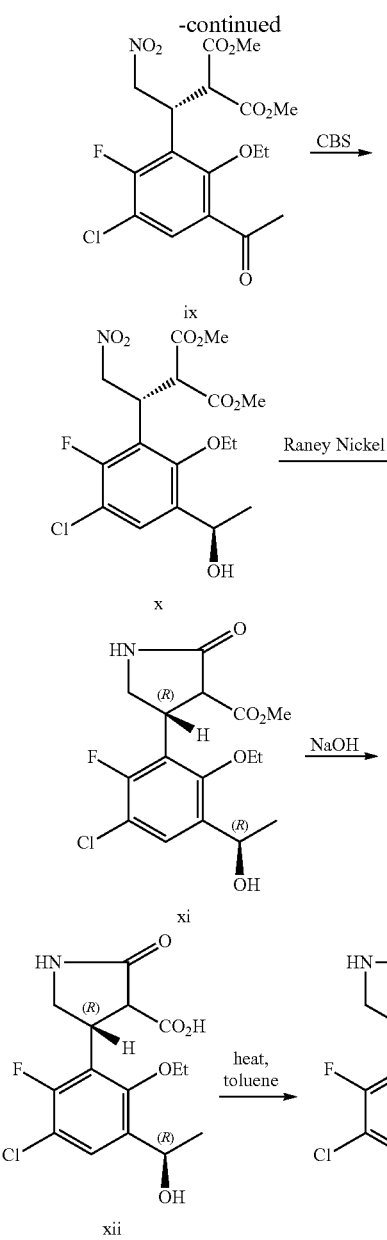

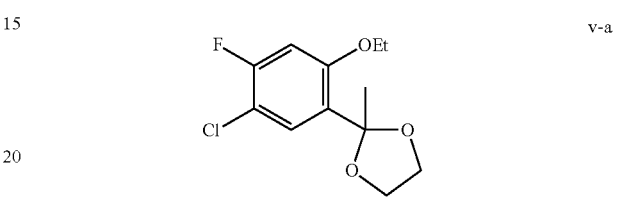

Step 1. 1-(5-chloro-2-ethoxy-4-fluorophenyl)ethanone (iv-a)

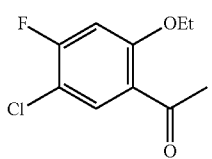

1-(5-Chloro-4-fluoro-2-hydroxyphenyl)ethanone (Compound ii from Example 1, Step 1, 1350 g, 7160 mmol), N,N-dimethylformamide (3.32 L), iodoethane (1340 g, 8590 mmol), and potassium carbonate (1980 g, 14300 mmol) were mixed together and stirred at room temperature for 45 min. The batch temperature went up to 55° C. from 22° C. The reaction mixture was heated to 60° C. for 1 h (the batch temperature reached 67° C. in 30 min and then dropped to 60° C.). HPLC analysis indicated all starting material was consumed. Water (10 L) was added in one portion (agitation will cease if water is added in portions). The resulting slurry was stirred at room temperature for 30 min. The product was collected by filtration and was rinsed with water (3 L). The product dried on the filter under vacuum for 5 days to give compound iv-a as a tan solid (1418 g). $^1$H NMR (400 MHz, DMSO-$d_6$) δ 7.69 (d, J=8.9 Hz, 1H), 7.30 (d, J=11.6 Hz, 1H), 4.15 (q, J=7.0 Hz, 2H), 2.51 (s, 3H), 1.37 (t, J=7.0 Hz, 3H).

Step 2. 2-(5-chloro-2-ethoxy-4-fluorophenyl)-2-methyl-1,3-dioxolane (v-a)

A solution of 1-(5-chloro-2-ethoxy-4-fluorophenyl)ethanone (iv-a, 1481.0 g, 6836.3 mmol) was dissolved in toluene (6 L). 1,2-Ethanediol (953 mL, 17100 mmol) and p-toluenesulfonic acid monohydrate (104 g, 547 mmol) were added to the solution. The reaction mixture was heated to reflux at 104-110° C. with the use of a Dean-Stark trap to remove the water for 17.4 h. HPLC analysis indicated 37% of starting material remained unreacted. About 600 mL of distillate was removed and the reaction mixture was heated under reflux for additional 5 h (total 22 h). HPLC analysis indicated no further reaction.

It was speculated that residual $K_2CO_3$ in the starting material compound iv-a may have halted the reaction. Therefore, the reaction mixture was cooled to room temperature and washed with 1 N aqueous hydrochloric acid (3×6.66 L). After the aqueous acid wash, the organic layer was transferred back to the reaction vessel. 1,2-Ethanediol (381 mL, 6840 mmol) and p-toluenesulfonic acid monohydrate (104 g, 547 mmol) were added and the reaction mixture was heated under reflux for 16 h. HPLC analysis indicated about 20% of starting material remained unreacted. About 100 mL of distillate was removed. 1,2-Ethanediol (380 mL, 6800 mmol) was added and refluxed for 6 h (22 h total). HPLC indicated 7% of starting material remained unreacted. About 125 mL of distillate was removed. The reaction mixture was heated to reflux for 6 h (total 28 h). HPLC indicated 5.4% of starting material remained unreacted. About 125 mL of distillate was removed. The reaction mixture was heated to reflux for additional 7 h. HPLC analysis indicated 3.5% of starting material remained unreacted. About 80 mL of distillate was removed. The reaction was deemed complete at this point.

The reaction mixture was washed with a 1 N aqueous sodium hydroxide solution (2×5.5 L). The first basic wash was extracted with toluene (2.1 L). The combined toluene solution was washed with water (7 L) and concentrated to give 2153 g of dark oil.

HPLC analysis indicated product purity at 93.8% with 1.90% of starting material and 0.79% of de-iodo product. 41 NMR analysis indicated about 0.5 equivalent of toluene (about 256 g) remained in the product. The corrected yield of compound v-a was 88.0%. $^1$H NMR (300 MHz, CDCl$_3$) δ 7.51 (d, J=8.8 Hz, 1H), 6.70 (d, J=11.0 Hz, 1H), 4.17-3.92 (m, 4H), 3.91-3.80 (m, 2H), 1.75 (s, 3H), 1.46 (t, J=7.0 Hz, 3H).

Step 3. 3-Chloro-6-ethoxy-2-fluoro-5-(2-methyl-1,3-dioxolan-2-yl)benzaldehyde (vi)

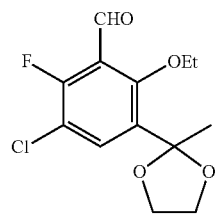

vi

Into an oven-dried 3-L 4-neck round bottom flask equipped with an overhead stirrer, a 500 mL addition funnel, nitrogen inlet, septa, and thermocouple was charged N,N-diisopropylamine (87.8 mL, 626 mmol) and anhydrous tetrahydrofuran (1090 mL, 13500 mmol). This solution was cooled to −72° C. and charged with 2.5 M n-butyllithium in hexanes (261 mL, 652 mmol). The n-butyllithium solution was added over 18 min. The maximum internal temperature during the addition was −65°. The dry ice-acetone bath was replaced with an ice-water bath and the reaction mixture was warmed to about −5° C. to about 0° C. and held for 15 min. The reaction mixture was then cooled to −74.5° C.

To a separate 1-L round bottom flask containing 2-(5-chloro-2-ethoxy-4-fluorophenyl)-2-methyl-1,3-dioxolane (v-a, 136.1 g, 522.1 mmol) was added anhydrous tetrahydrofuran (456 mL) to dissolve the solids. The resulting solution was cooled in an ice bath to about 0° C. The solution containing compound v-a was transferred to the LDA solution over 40 minutes via a canula while maintaining the reaction temperature between −70° C. and −72.5° C. The reaction mixture became yellow slurry and was stirred for 37 min at −74° C. N,N-Dimethylformamide (60.6 mL, 783 mmol) was charged in one portion via a syringe and this addition produced an exotherm from −74.5° C. to −66.5° C.

The reaction was monitored by HPLC at 90 min after the addition. The starting material was present at 2.9%. The cold bath was removed and the reaction mixture was warmed in ambient temperature. The reaction mixture was sampled and analyzed after 3 h and unreacted starting material was present at 1.5%. The reaction was deemed complete and was quenched by addition of the reaction solution to ice water (1.4 L) and diluted with ethyl acetate (1.5 L). The aqueous layer was extracted with ethyl acetate (1.5 L) and the organic layers were combined and washed with brine (20% w/w aq. NaCl, 2×600 mL) and dried over anhydrous $MgSO_4$. The $MgSO_4$ was removed by filtration and the filtrate was concentrated to an oil with some solids present. This residue was dissolved in methylene chloride and loaded onto a pad of silica gel (586 g). The silica pad was eluted with 2% EtOAc/DCM (monitored by TLC using 100% DCM as eluent). The desired fractions were collected and concentrated under reduced pressure to give a light amber oil. The oil was placed under high vacuum to give compound vi as a yellow solid (146.5 g, 95.1% yield). $^1$H NMR (400 MHz, $CDCl_3$) δ 10.27 (s, 1H), 7.78 (d, J=8.5 Hz, 1H), 4.10-3.96 (m, 4H), 3.87-3.76 (m, 2H), 1.72 (s, 3H), 1.44 (t, J=7.0 Hz, 3H). LCMS for $C_{13}H_{15}ClFO_4$ (M+H)$^+$: m/z=289.1.

Steps 4-10. (R)-4-(3-chloro-6-ethoxy-2-fluoro-5-((R)-1-hydroxyethyl)phenyl)pyrrolidin-2-one (xiii)

The title compound was prepared using procedures analogous to those described in Example 1, Steps 6-12.

Example 3

(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloride

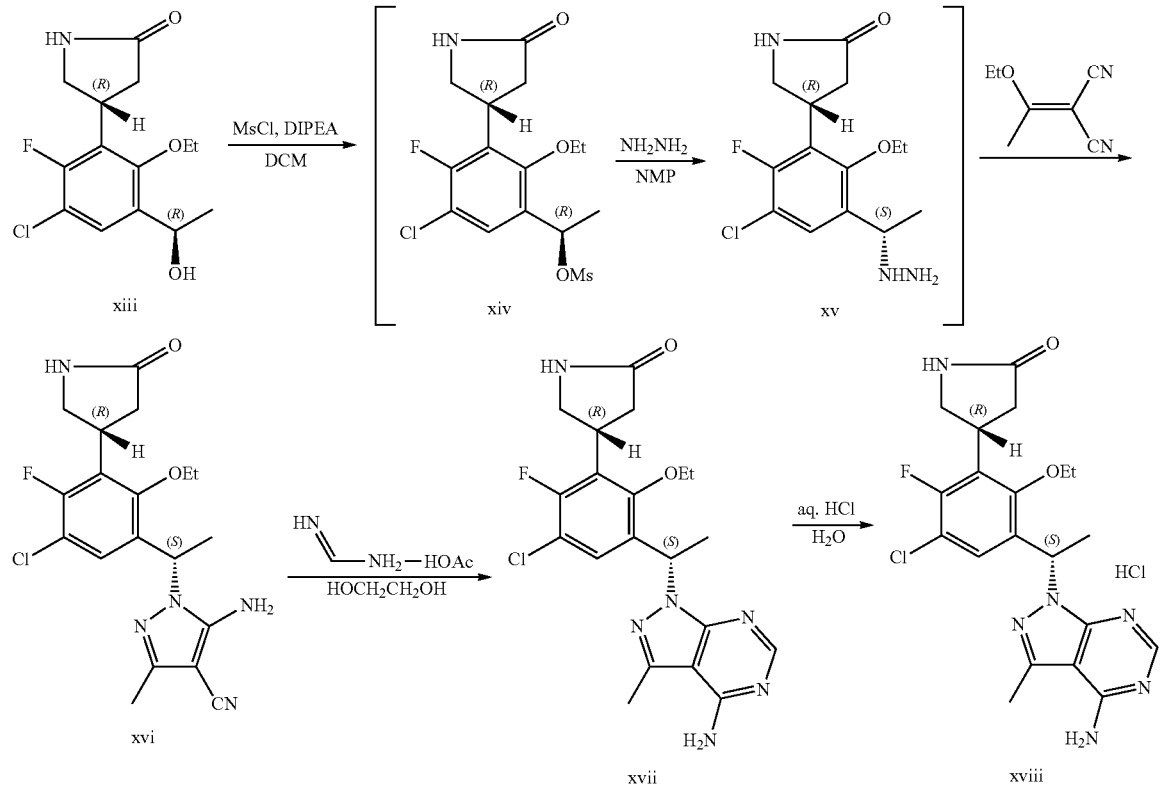

Step 1. (R)-1-(5-chloro-2-ethoxy-4-fluoro-3-((R)-5-oxopyrrolidin-3-yl)phenyl)ethylmethanesulfonate (xiv)

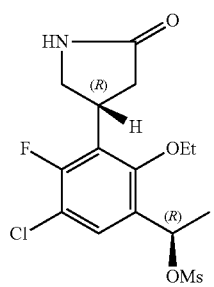

xiv (R)-4-(3-Chloro-6-ethoxy-2-fluoro-5-((R)-1-hydroxyethyl)phenyl)pyrrolidin-2-one (xiii, 172.0 g, 570.0 mmol) (consisted of 147 g at 99.83%: 0.09% chiral purity, 99.33% chemical purity; and 25 g, 87.46%: 12.54% chiral purity, 86.74% chemical purity) was dissolved in methylene chloride (860 mL). N,N-diisopropylethylamine (149 mL, 855 mmol) was added to the solution at from about −7° C. to about 2° C. Methanesulfonyl chloride (57.4 mL, 741 mmol) was added dropwise to the reaction mixture over 25 min. The suspension turned into a clear solution. At 30 min reaction time point HPLC indicated the reaction was complete. This reaction mixture containing compound xiv was used directly in the next reaction.

Step 2. (R)-4-(3-chloro-6-ethoxy-2-fluoro-5-((S)-1-hydrazinylethyl)phenyl)pyrrolidin-2-one (xv)

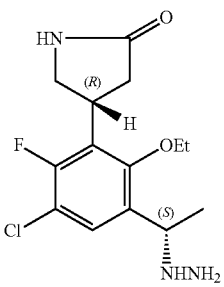

xv

At 0° C., hydrazine (178.9 mL, 5.7 mol) was added in one portion followed by N-methylpyrrolidinone (860 mL) to the reaction mixture containing compound xiv from Step 1. The reaction mixture turned cloudy and some precipitates formed. The mixture was heated to 40-57° C. under nitrogen for 90 min. HPLC indicated all the mesylate had been consumed.

The reaction mixture was cooled to room temperature and a saturated solution of sodium bicarbonate (28.3 g) in water (300 mL) was added. The mixture was stirred for 20 min, at which time dichloromethane (300 mL) was added. The organic layer was separated and stirred with a solution of sodium bicarbonate (14.2 g) in water (150 mL). The aqueous layer was extracted with dichloromethane (200 mL×2). The combined organic layers were washed with brine (80 mL), dried over anhydrous $Na_2SO_4$ (311 g), concentrated, and azeotroped with toluene (250 mL) to give a colorless N-methylpyrrolidinone solution containing compound xv which was used directly in the next reaction. A sample was purified for NMR analysis. $^1$H NMR (400 MHz, DMSO-$d_6$), δ 7.88 (s, 1H), 7.66 (d, J=8.5 Hz, 1H), 4.42 (q, J=6.7 Hz, 1H), 4.06-3.88 (m, 2H), 3.79-3.66 (m, 1H), 3.65-3.51 (m, 1H), 3.24 (t, J=8.8 Hz, 1H), 2.60-2.46 (m, 1H), 2.36-2.25 (m, 1H), 1.37 (t, J=6.9 Hz, 3H), 1.26 (d, J=6.8 Hz, 3H). LCMS for $C_{14}H_{19}ClFN_3O_2$ (M+H)$^+$: m/z=316.1.

Step 3. 5-Amino-1-((S)-1-(5-chloro-2-ethoxy-4-fluoro-3-((R)-5-oxopyrrolidin-3-yl)phenyl)ethyl)-3-methyl-1H-pyrazole-4-carbonitrile (xvi)

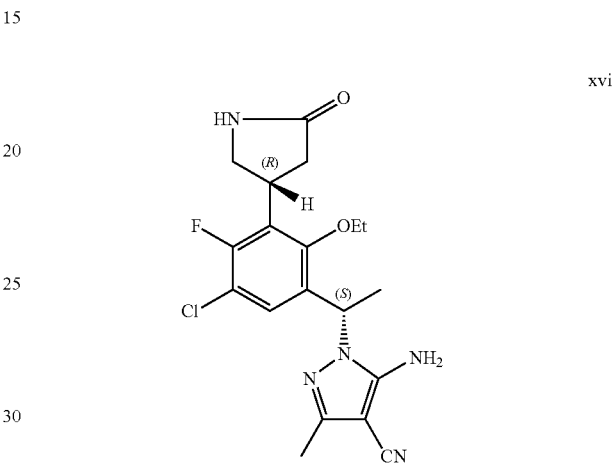

xvi

With stirring, (1-ethoxyethylidene)malononitrile (101 g, 741 mmol) was added to the N-methylpyrrolidinone solution of compound xv from Step 2, in portions and the mixture was stirred at room temperature under nitrogen. After 15 min, HPLC analysis indicated 11% starting material hydrazine, compound xv, relative to product compound xvi. N,N-Diisopropylethylamine (15 mL, 86 mmol) was added and the reaction mixture was stirred at room temperature for 15 h. HPLC analysis indicated 5.6% of starting material remained. N,N-Diisopropylethylamine (5 mL, 30 mmol) was added and the reaction mixture was stirred at room temperature for 5 h. HPLC indicated 5.6% starting material remained. The reaction mixture was stirred for 2.5 days and combined with two similar batches and worked up together.

The reaction mixtures of three batches of compound xvi were combined. An aqueous 0.5 M sodium hydroxide solution (3.8 L) was added at 10-20° C. and stirred for 5 min. HPLC indicated that all starting material (1-ethoxyethylidene)malononitrile was consumed. Ethyl acetate (4.0 L) was added and the mixture was stirred for 15 min. The layers were separated. The organic layer was washed with 0.5 M sodium hydroxide in water (2.38 L). The layers were separated. The combined aqueous layer was extracted with ethyl acetate (2×2 L). The combined organic layers were washed with 1.0 M aqueous hydrochloric acid (3.56 L) and the pH of the resulting aqueous layer was 2-3. The organic layer was washed with brine (5 L), dried over anhydrous $Na_2SO_4$, concentrated, and dried under high vacuum for 40 h to give compound xvi as a light brown foamy solid (702.7 g). $^1$H NMR (500 MHz, DMSO-$d_6$) δ 7.78 (s, 1H), 7.44 (d, J=8.4 Hz, 1H), 6.53 (s, 2H), 5.64 (q, J=6.7 Hz, 1H), 3.96 (m, 1H), 3.74 (m, 1H), 3.34 (m, 1H), 3.58 (m, 2H), 2.59-2.50 (m, 1H), 2.29 (m, 1H), 2.04 (s, 3H), 1.57 (d, J=6.8 Hz, 3H), 1.37 (t, J=6.9 Hz, 3H). LCMS for $C_{19}H_{22}ClFN_5O_2$ (M+H)$^+$: m/z=406.1.

The overall yield of compound xvi three steps (mesylation, hydrazinolysis and pyrazole formation) was calculated to be 72.8% from the total input of compound xiii. The purity was determined by HPLC to be about 80%. HPLC analysis indicated some product existing in the basic aqueous layer which was subsequently extracted with EtOAc (2 L), washed with 1.0 M aqueous hydrochloric acid and brine, dried with anhydrous sodium sulfate, concentrated, and dried on high vacuum pump for 40 h to afford compound xvi as a brown oil (134 g, 13.9%).

Step 4. (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (xvii)

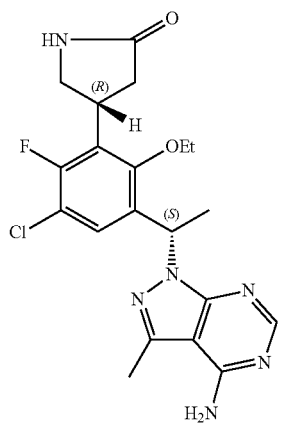

xvii

5-Amino-1-((S)-1-(5-chloro-2-ethoxy-4-fluoro-3-((R)-5-oxopyrrolidin-3-yl)phenyl)ethyl)-3-methyl-1H-pyrazole-4-carbonitrile (xvi, 702.7 g, 1731 mmol) was added to a reaction vessel with formamidine acetate (1802 g, 17.31 mol) and 1,2-ethanediol (3.51 L). The reaction mixture was heated at 102-103° C. with stirring for 18 h. The reaction mixture was cooled to room temperature and ethyl acetate (7 L) and water (6 L) were added and the biphasic mixture was stirred for 15 min. The organic layer was separated and the aqueous layer was diluted with additional water (4.5 L) and ethyl acetate (3 L) and stirred for 10 min. The organic layer was separated. The aqueous layer was further extracted with ethyl acetate (2 L). The organic layers were combined and stirred with water (4.5 L). The aqueous layer was separated and the organic layer was filtered through a pad of celite (about 1 kg). The organic layer was extracted with 1.0 M aqueous hydrochloric acid (7 L) by stirring the mixture for 10 min. The aqueous layer was separated. The clear brown organic layer was stirred with additional 1.0 M aqueous hydrochloric acid (3 L) for 10 min. The aqueous layer was separated. The aqueous acidic layers were combined and washed with toluene (500 mL). The aqueous acidic solution was cooled with an ice-water bath and methylene chloride (4 L) was added. At 5-15° C., a solution of sodium hydroxide (530 g) in water (530 mL) (50% NaOH solution) was added slowly until to a solution pH of 11-12. Solid precipitates were observed. Additional methylene chloride (3.5 L) and methanol (300 mL) were added and the mixture was stirred for 10-15 min. The solid product was collected by filtration and dried on the filter under suction for 16 h to give compound xvii (289.7 g) as a brown solid. $^1$H NMR (400 MHz, DMSO-d$_6$) δ 8.11 (s, 1H), 7.82 (s, 1H), 7.52 (d, J=8.5 Hz, 1H), 7.30 (br s, 2H), 6.23 (q, J=7.0 Hz, 1H), 3.97 (p, J=9.2 Hz, 1H), 3.90-3.73 (m, 2H), 3.57 (t, J=9.9 Hz, 1H), 3.25 (dd, J=9.2, 8.7 Hz, 1H), 2.48 (s, 3H), 2.60-2.50 (m, 1H), 2.36-2.20 (m, 1H), 1.69 (d, J=7.1 Hz, 3 H), 1.39 (t, J=6.9 Hz, 3H). LCMS for $C_{20}H_{23}ClFN_6O_2$ (M+H)$^+$: m/z=433.3.

The filtrate was transferred into a separatory funnel and the organic layer was separated. The aqueous layer was stirred with methylene chloride (5 L) and methanol (200 mL). The combined organic layer was dried over anhydrous sodium sulfate, concentrated, dried on high vacuum pump for 16 h to give additional amount 259.3 g as a brown solid. The total yield of xvii was 548.3 g in 73.2% yield.

Step 5. (R)-4-(3-((S)-1-(4-Amino-3-methyl-1H-pyrazolo[3,4-d]pyrimidin-1-yl)ethyl)-5-chloro-2-ethoxy-6-fluorophenyl)pyrrolidin-2-one hydrochloride salt (xviii)

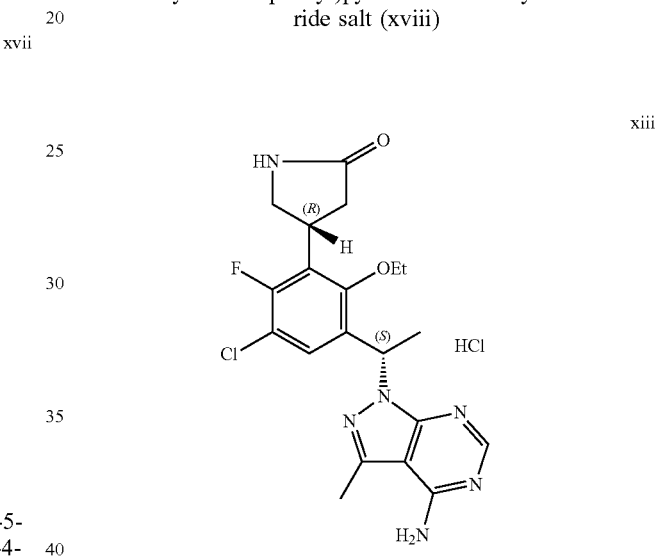

xiii

A 1.0 M aqueous hydrochloric acid (HCl, 5.0 L, 5.0 mol) solution was added to (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (xvii, 609.8 g, 1.409 mol) at room temperature. The resulting thick slurry was then heated to 50° C. to afford a clear solution. An additional 1.82 L of 1.0 M aqueous hydrochloric acid solution (HCl, 1.82 L, 1.82 mol; total 6.82 L, 6.82 mol, 4.84 equiv) was added to the clear solution at 50° C. and the solution was then filtered through a polish filter at approximately 50° C. The polish filtered reaction mixture was gradually cooled to room temperature over 2 h before it was further cooled to 0-5° C. The reaction mixture was stirred at 0-5° C. for at least 20 min to initiate precipitation. The resulting solids were collected by filtration, rinsed with a portion of cold mother liquor, followed by 1.0 M aqueous hydrochloric acid (HCl, 200 mL), and dried on the filter funnel at room temperature under suction to constant weight (in about 39 h) to afford the hydrochloric acid salt of the compound of Formula I: (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloride (xviii, 348.7 g, 661.2 g theoretical, 52.7%) as white crystalline powder. $^1$H NMR (400 MHz, DMSO-d$_6$) δ 9.39 (br s, 1H), 9.05 (br s, 1H), 8.50 (s, 1H), 7.84 (s, 1H), 7.59 (d, J=8.4 Hz, 1H), 6.28 (q, J=6.9 Hz, 1H), 3.95 (m, 1H), 3.79

(m, 2H), 3.55 (m, 1H), 3.22 (m, 1H), 2.59 (s, 3H), 2.55 (ddd, J=16.8, 10.3, 2.3 Hz, 1H), 2.28 (ddd, J=16.8, 8.6, 1.5 Hz, 1H), 1.73 (d, J=7.0 Hz, 3H), 1.38 (t, J=6.9 Hz, 3H) ppm. $^{13}$C NMR (100 MHz, DMSO-$d_6$) δ 175.3, 156.4 ($J_{CF}$=249.8 Hz), 153.8 ($J_{CF}$=7.0 Hz), 152.4, 150.8, 147.3, 144.3, 131.4 ($J_{CF}$=3.5 Hz), 127.3, 126.4 ($J_{CF}$=12.6 Hz), 116.1 ($J_{CF}$=18.4 Hz), 98.0, 72.1, 49.1, 46.6, 36.0, 29.4, 21.0, 15.4, 14.6 ppm. $^{19}$F NMR (376 MHz, DMSO-$d_6$) δ −113.6 (d, $J_{FH}$=7.7 Hz) ppm. $C_{20}H_{23}Cl_2FN_6O_2$ (MW 469.34); LCMS (EI) m/e 433.2 (M$^+$+H; exact mass of xvii: 432.15). Water content by KF: 3.63% by weight; Chloride (Cl$^-$) content by titration: 7.56% by weight (7.56% by theory).

The melting/decomposition range of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloride salt crystalline form was determined by DSC, from an initial temperature of 30° C. to a final temperature of 350° C. using a heating rate of 10° C./min. The DSC thermogram revealed one endothermic event with an onset at 194.37° C. and the peak at 206.55° C., as shown in FIG. 1.

The TGA thermogram showed the total weight loss of 4.3% up to 210° C. Above 210° C. the salt starts to decompose, as shown in FIG. 2.

A representative X-Ray Power Diffraction (XRPD) pattern is shown in FIG. 3 and Table 2 shows the corresponding peaks and intensities.

TABLE 2

| 2-theta | Relative Intensity |
| --- | --- |
| 5.739 | 2.20% |
| 7.133 | 1.20% |
| 7.736 | 0.10% |
| 10.225 | 2.30% |
| 11.283 | 99.00% |
| 11.303 | 94.10% |
| 13.666 | 2.90% |
| 14.166 | 0.90% |
| 14.833 | 0.10% |
| 15.364 | 3.80% |
| 16.354 | 9.70% |
| 17.136 | 0.50% |
| 16.866 | 2.70% |
| 17.435 | 5.50% |
| 17.635 | 3.30% |
| 18.811 | 5.10% |
| 18.898 | 6.60% |
| 19.603 | 1.50% |
| 20.157 | 1.80% |
| 20.593 | 0.50% |
| 21.039 | 11.10% |
| 21.308 | 3.80% |
| 22.169 | 7.50% |
| 23.002 | 11.50% |
| 24.628 | 6.60% |
| 25.098 | 2.20% |
| 25.66 | 7.00% |
| 25.895 | 4.00% |
| 27.168 | 3.10% |
| 27.792 | 8.50% |
| 28.1 | 10.00% |
| 28.464 | 5.50% |
| 30.134 | 3.20% |
| 31.239 | 13.70% |
| 31.918 | 1.30% |
| 32.827 | 9.50% |
| 33.818 | 0.70% |
| 34.198 | 2.80% |
| 35.033 | 2.10% |
| 35.423 | 2.10% |
| 36.226 | 0.30% |
| 36.676 | 0.90% |
| 37.47 | 0.90% |

TABLE 2-continued

| 2-theta | Relative Intensity |
| --- | --- |
| 37.951 | 0.50% |
| 38.457 | 1.70% |
| 39.055 | 0.20% |
| 39.968 | 0.20% |
| 40.184 | 0.30% |
| 40.962 | 0.20% |
| 42 | 1.30% |
| 42.916 | 2.40% |
| 43.373 | 0.50% |
| 44.148 | 0.40% |
| 45.29 | 0.30% |
| 46.089 | 1.40% |
| 47.572 | 0.40% |
| 48.897 | 0.70% |
| 49.647 | 0.50% |
| 50.589 | 0.30% |
| 51.042 | 0.10% |
| 51.687 | 0.40% |
| 52.624 | 0.40% |
| 53.287 | 0.50% |
| 54.104 | 0.20% |
| 54.127 | 0.10% |
| 54.159 | 0.20% |
| 55.42 | 0.30% |
| 56.821 | 0.10% |

Example 4

Alternative Synthesis of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloride

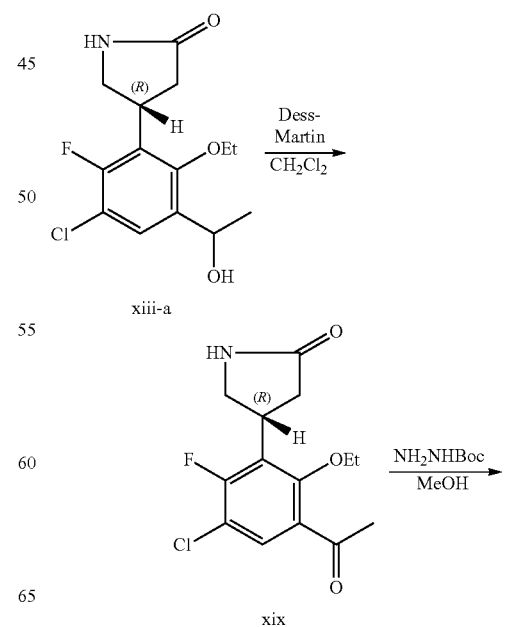

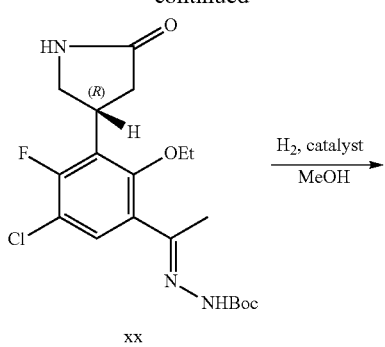

xx

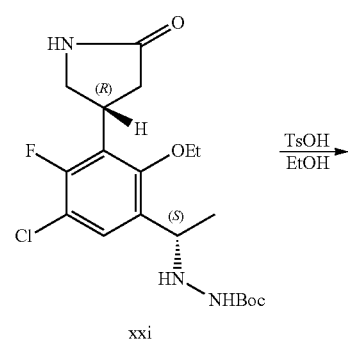

xxi

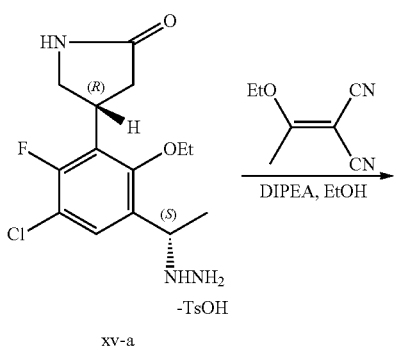

xv-a

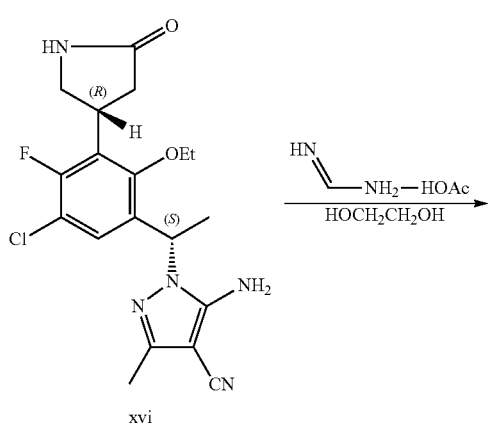

xvi

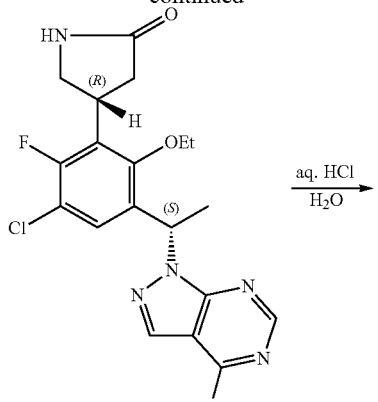

xvii

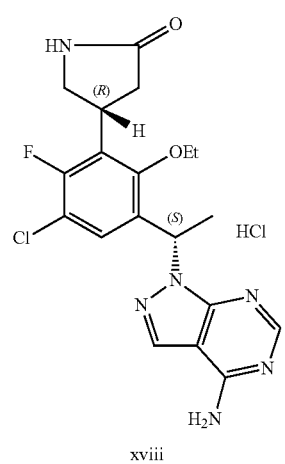

xviii

Step 1. (R)-4-(3-acetyl-5-chloro-2-ethoxy-6-fluoro-phenyl)pyrrolidin-2-one (xix)

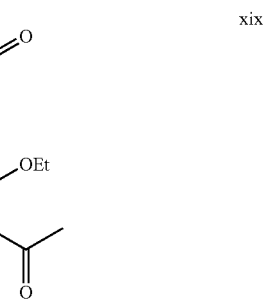

xix (4R)-4-[3-Chloro-6-ethoxy-2-fluoro-5-(1-hydroxyethyl) phenyl]pyrrolidin-2-one (as a mixture of two diastereomers with R-configuration at the pyrrolidinone and R- or S-configurations at the secondary alcohol) (xiii, 16.7 g, 55.3 mmol) was dissolved in dichloromethane (167 mL). The solution was cooled in an ice-water bath and Dess-Martin periodinane (35.2 g, 83.0 mmol) was added in small portions. The reaction mixture was stirred at room temperature for 2 h, at which time HPLC analysis showed reaction completion. A solution of sodium sulfite (28 g, 220 mmol) in water (70 mL) was added to the reaction mixture and the mixture was stirred for 20 min. A 1.0 M sodium hydroxide solution was added to the mixture and stirred for 10 min. The layers were allowed to settle and the organic layer was separated and washed sequentially with 1 M aqueous sodium hydroxide solution (66 mL) and water (60 mL). The organic layer was dried over anhydrous sodium sulfate. The drying agent was removed by filtration and the filtrate was concentrated to give (R)-4-[3-acetyl-5-chloro-2-ethoxy-6-fluorophenyl]pyrrolidin-2-one as an oil which was used in the next reaction without further purification.

Step 2. (R,E)-tert-butyl 2-(1-(5-chloro-2-ethoxy-4-fluoro-3-(5-oxopyrrolidin-3-yl)phenyl)ethylidene)hydrazinecarboxylate (xx)

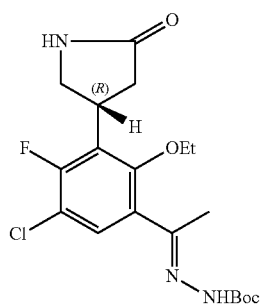

xx

Crude (R)-4-[3-acetyl-5-chloro-2-ethoxy-6-fluorophenyl] pyrrolidin-2-one (compound xix from Step 1) was dissolved in methanol (60 mL) and t-butyl carbazate (8.04 g, 60.8 mmol) was added to the solution. The reaction mixture was stirred at 65° C. for 3.5 days, at which time HPLC analysis showed reaction completion. The mixture was concentrated under reduced pressure and the residue was purified by silica gel chromatography eluting with a mixture of 0-5% of methanol in ethyl acetate to give (R,E)-tert-butyl 2-(1-(5-chloro-2-ethoxy-4-fluoro-3-(5-oxopyrrolidin-3-yl)phenyl)ethylidene)hydrazinecarboxylate (xx, 19.5 g, 85%). $^1$H NMR (500 MHz, DMSO-$d_6$) δ 9.83 (s, 1H), 7.78 (s, 1H), 7.36 (d, J=8.6 Hz, 1H), 4.07 (p, J=9.1 Hz, 1H), 3.84-3.69 (m, 2H), 3.59 (t, J=9.5 Hz, 1H), 3.28 (t, J=9.5 Hz, 1H), 2.54 (m, 1H), 2.33 (m, 1H), 2.14 (s, 3H), 1.46 (s, 9H), 1.25 (t, J=7.0 Hz, 3H). LCMS for $C_{19}H_{25}ClFN_3NaO_4$ (M+Na)$^+$: m/z=436.1.

Step 3. tert-Butyl 2-((S)-1-(5-chloro-2-ethoxy-4-fluoro-3-((R)-5-oxopyrrolidin-3-yl)phenyl)ethyl)hydrazinecarboxylate (xxi)

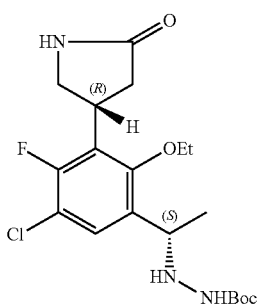

xxi (R,E)-tert-butyl 2-(1-(5-chloro-2-ethoxy-4-fluoro-3-(5-oxopyrrolidin-3-yl)phenyl)ethylidene)hydrazinecarboxylate (xx, 0.5 g, 1.2 mmol) was dissolved in methanol (25 mL) and the solution was bubbled with nitrogen gas for 5 min. Bis(1,5-cyclooctadiene)rhodium(I)tetrafluoroborate (35 mg, 0.086 mmol) and (R)-(-)-1-{(S)-2-[bis(4-trifluoromethylphenyl)phosphine]ferrocenyl}ethyl-di-t-butylphosphine (64 mg, 0.094 mmol) were added to the solution and the resulting reaction mixture was bubbled with nitrogen gas for 30 min. The reaction mixture was then agitated under hydrogen gas (56 psi) pressure for 2.5 days. The reaction mixture was concentrated under reduced pressure and the resulting residue was purified by silica gel column chromatography eluting with a mixture of methanol (0-10%) in ethyl acetate. The desired fractions were concentrated to give tert-butyl 2-((S)-1-(5-chloro-2-ethoxy-4-fluoro-3-((R)-5-oxopyrrolidin-3-yl)phenyl)ethyl)hydrazinecarboxylate (xxi, 428 mg, 85% yield). $^1$H NMR (500 MHz, DMSO-$d_6$) δ 8.18 (s, 1H), 7.78 (s, 1H), 7.53 (d, J=8.2 Hz, 1H), 4.73 (s, 1H), 4.41 (br s, 1H), 3.98 (m, 1H), 3.75 (m, 2H), 3.61 (m, 1H), 3.26 (m, 1H), 2.53 (m, 1H), 2.29 (dd, J=17.6, 8.6 Hz, 1H), 1.32 (s, 12H), 1.10 (d, J=6.5 Hz, 1H). LCMS for $C_{19}H_{27}ClFN_3NaO_4$ (M+Na): m/z=437.9. Chiral HPLC analysis indicated the product contained the desired diastereomer tert-butyl-2-((S)-1-(5-chloro-2-ethoxy-4-fluoro-3-((R)-5-oxopyrrolidin-3-yl)phenyl)ethyl)hydrazine carboxylate (xxi) at 85.6% and the undesired diastereomer tert-butyl-2-((R)-1-(5-chloro-2-ethoxy-4-fluoro-3-((R)-5-oxopyrrolidin-3-yl)phenyl)ethyl)hydrazinecarboxylate at 14.3%.

Step 4. 5-Amino-1-((S)-1-(5-chloro-2-ethoxy-4-fluoro-3-((R)-5-oxopyrrolidin-3-yl)phenyl)ethyl)-3-methyl-1H-pyrazole-4-carbonitrile (xvi)

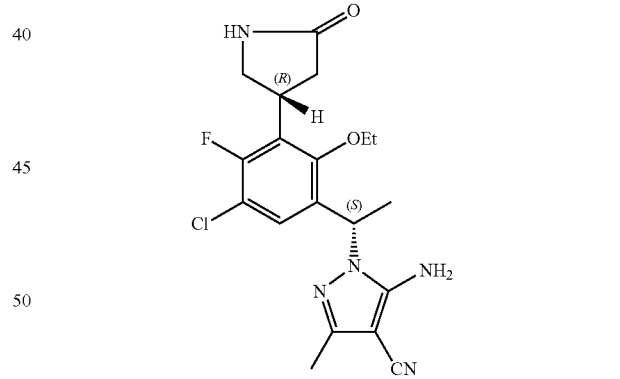

xvi tert-Butyl 2-((S)-1-(5-chloro-2-ethoxy-4-fluoro-3-((R)-5-oxopyrrolidin-3-yl)phenyl)ethyl)hydrazinecarboxylate (xxi, 130 mg, 0.31 mmol) and p-toluenesulfonic acid monohydrate (86 mg, 0.45 mmol) were added to ethanol (3 mL) and the reaction mixture was heated at 50° C. for 20 h. HPLC analysis showed there was about 88% of unreacted starting material. Additional amount of p-toluene sulfonic acid (86 mg, 0.45 mmol) was charged and the reaction mixture was heated to 60° C. for 24h. HPLC analysis showed complete Boc-deprotection. This reaction mixture was added with (1-ethoxyethylidene)malononitrile (61 mg, 0.45 mmol) and N,N-diisopropylethylamine (260 μL, 1.5 mmol). The reaction mixture was stirred at room temperature for 2 h. HPLC showed completion of pyrazole-ring formation. 1.0 M aqueous sodium hydroxide solution was added to the reaction mixture and stirred for 20 min. Ethyl acetate (20 mL) was added to the mixture and stirred. The biphasic mixture was allowed to settle. The ethyl acetate layer was collected and the aqueous layer was extracted with ethyl acetate (10 mL). The combined ethyl acetate solution was added with 1M aqueous hydrochloric acid (5 mL) and stirred for 15 min. The biphasic mixture was allowed to settle and the organic layer was collected and dried over anhydrous sodium sulfate. Sodium sulfate was removed by filtration and to filtrate was concentrated to give 5-Amino-1-((S)-1-(5-chloro-2-ethoxy-4-fluoro-3-((R)-5-oxopyrrolidin-3-yl)phenyl)ethyl)-3-methyl-1H-pyrazole-4-carbonitrile (xvi, 126 mg, quantitative yield of crude product) and was used in the next step without further purification.

Step 5. (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (xvii)

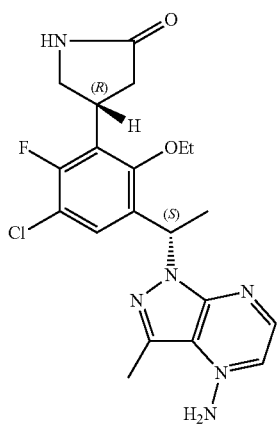

xvii

5-Amino-1-{(1S)-1-[5-chloro-2-ethoxy-4-fluoro-3-(5-oxopyrrolidin-3-yl)phenyl]ethyl}-3-methyl-1Hpyrazole-4-carbonitrile (xvi, 126 mg, 0.31 mmol) was added with formamidine acetate (323 mg, 3.1 mmol) and 1,2-ethanediol (2 mL). The reaction mixture was heated at 104-105° C. with stirring. After 18 h, HPLC analysis showed about 44% of starting material compound xvi remaining. The reaction mixture was heated to 115° C. for 24 h. HPLC analysis showed the reaction was complete. The reaction mixture was cooled to room temperature and ethyl acetate (10 mL) and water (5 ml) were added. The biphasic mixture was stirred. The layers were allowed to separate. The organic layer was collected and the aqueous layer was extracted with ethyl acetate (5 mL). The combined ethyl acetate solution was washed with water (5 mL), dried over anhydrous sodium sulfate. Sodium sulfate was removed by filtration and the filtrate was concentrated to a residue. The residue was purified by silica gel chromatography. The column was eluted with a mixture of methanol (0-5%) in methylene chloride. The desired fractions were combined and evaporated to give (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (xvii, 94 mg, 69.9% yield). $^1$H NMR (400 MHz, DMSO-d$_6$) δ 8.11 (s, 1H), 7.82 (s, 1H), 7.52 (d, J=8.5 Hz, 1H), 7.30 (br s, 2H), 6.23 (q, J=7.0 Hz, 1H), 3.97 (p, J=9.2 Hz, 1H), 3.90-3.73 (m, 2H), 3.57 (t, J=9.9 Hz, 1H), 3.25 (dd, J=9.2, 8.7 Hz, 1H), 2.48 (s, 3H), 2.60-2.50 (m, 1H), 2.36-2.20 (m, 1H), 1.69 (d, J=7.1 Hz, 3 H), 1.39 (t, J=6.9 Hz, 3H). LCMS for $C_{20}H_{23}ClFN_6O_2$ (M+H)$^+$: m/z=433.3.

Chiral HPLC analysis of the product indicated that it contained the desired diastereomer, (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (xvii), at 87% and the undesired diastereomer (R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one at 13%.

Step 6. (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloride The title product was prepared according to the procedure described in Example 3, Step 5. The resulting hydrochloride salt matches well with the material made from the synthetic process described in Example 3, in every comparable aspect including chemical purity, chiral purity, and solid state characteristics.

Example A1

PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5) P3 Detector Protein is purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) is purchased from Millipore (Bedford, Mass.). ATP, MgCl$_2$, DTT, EDTA, HEPES and CHAPS are purchased from Sigma-Aldrich (St. Louis, Mo.).

AlphaScreen™ Assay for PI3Kδ

The kinase reaction are conducted in 384-well REMP plate from Thermo Fisher Scientific in a final volume of 40 µL. Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5mM MgCl$_2$, 50 mM NaCl, 5 mM DTT and CHAPS 0.04%. Reactions are initiated by the addition of ATP, the final reaction mixture consisted of 20 µM PIP2, 20 µM ATP, 1.2 nM PI3Kδ are incubated for 20 minutes. 10 µL of reaction mixture are then transferred to 5 µL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 µL AlphaScreen™ donor and acceptor beads suspended in quench buffer containing 25 nM PI(3,4,5)P3 detector protein. The final concentration of both donor and acceptor beads is 20 mg/ml. After plate sealing, the plate are incubated in a dark location at room temperature for 2 hours. The activity of the product is determined on Fusion-alpha microplate reader (Perkin-Elmer). IC$_{50}$ determination is performed by fitting the curve of percent control activity versus the log of the inhibitor concentration using the GraphPad Prism 3.0 software.

Example A2

PI3K Enzyme Assay

Materials: Lipid kinase substrate, phosphoinositol-4,5-bisphosphate (PIP2), are purchased from Echelon Biosciences (Salt Lake City, Utah). PI3K isoforms α, β, δ and γ are purchased from Millipore (Bedford, Mass.). ATP, MgCl$_2$, DTT, EDTA, MOPS and CHAPS are purchased from Sigma-Aldrich (St. Louis, Mo.).

The kinase reactions are conducted in clear-bottom 96-well plate from Thermo Fisher Scientific in a final volume of 24 μL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM MgCl$_2$, 5 mM DTT and CHAPS 0.03%. The reaction mixture is prepared containing 50 μM PIP2, kinase and varying concentration of inhibitors. Reactions are initiated by the addition of ATP containing 2.2 μCi [γ-$^{33}$P]ATP to a final concentration of 1000 μM. The final concentration of PI3K isoforms α, β, δ and γ in the assay were 1.3, 9.4, 2.9 and 10.8 nM, respectively. Reactions are incubated for 180 minutes and terminated by the addition of 100 μL of 1 M potassium phosphate pH 8.0, 30 mM EDTA quench buffer. A 100 μL aliquot of the reaction solution are then transferred to 96-well Millipore MultiScreen IP 0.45 μm PVDF filter plate (The filter plate is prewetted with 200 μL 100% ethanol, distilled water, and 1 M potassium phosphate pH 8.0, respectively). The filter plate is aspirated on a Millipore Manifold under vacuum and washed with 18×200 μL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 μL Microscint 20 scintillation cocktail (Perkin Elmer) in each well. After the plate sealing, the radioactivity of the product is determined by scintillation counting on Topcount (Perkin-Elmer). IC$_{50}$ determination is performed by fitting the curve of percent control activity versus the log of the inhibitor concentration using the GraphPad Prism 3.0 software.

The (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt was tested in the assay of Example A2 and determined to be a selective inhibitor for PI3Kδ.

The (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt was tested in the assay of Example A2 and determined to be a >100 fold selective inhibitor for PI3Kδ over each of PI3Kα, PI3Kβ, and PI3Kγ.

Example A3

PI3Kδ Scintillation Proximity Assay

Materials

[γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P] ATP, 4 nM PI3Kδ. Reactions were incubated for 210 min and terminated by the addition of 40 μL SPA beads suspended in quench buffer: 150mM potassium phosphate pH 8.0, 20% glycerol. 25 mM EDTA, 400 μM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. The compound of Formula I was found have an IC$_{50}$ of ≤10 nM in the assay of Example A3.

Example B1

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells (2×10$^5$/well/200 μL) are cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.) in the presence of different amount of test compounds for three days. [$^3$H]-thymidine (1 μCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example B2

Pfeiffer Cell Proliferation Assay

Pfeiffer cell line (diffuse large B cell lymphoma) are purchased from ATCC (Manassas, Va.) and maintained in the culture medium recommended (RPMI and 10% FBS). To measure the anti-proliferation activity of the compounds, the Pfeiffer cells are plated with the culture medium (2×10$^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS is then added to the cell culture for an additional 12 hours before the incorporated radioactivity is separated by filtration with water through GF/B filters (Packard Bioscience, Meridenj, Conn.) and measured by liquid scintillation counting with a TopCount (Packard Bioscience).

Example B3

SUDHL-6 Cell Proliferation Assay

SUDHL-6 cell line (diffuse large B cell lymphoma) was purchased from ATCC (Manassas, Va.) and maintained in the culture medium recommended (RPMI and 10% FBS). To measure the anti-proliferation activity of the compounds through ATP quantitation, the SUDHL-6 cells was plated with the culture medium (5000 cells/well/per 200 μl) into 96-well polystyrene clear black tissue culture plate (Greiner-bio-one through VWR, NJ) in the presence or absence of a concentration range of test compounds. After 3 days, Cell Titer-GLO Luminescent (Promega, Madison, Wis.) cell culture agent was added to each well for 10 minutes at room temperature to stabilize the luminescent signal. This determines the number of viable cells in culture based on quantitation of the ATP present, which signals the presence of metabolically active cells. Luminescence was measured with the TopCount 384 (Packard Bioscience through Perkin Elmer, Boston, Mass.).

Example C

Akt Phosphorylation Assay

Ramos cells (B lymphocyte from Burkitts lymphoma) are obtained from ATCC (Manassas, Va.) and maintained in RPMI1640 and 10% FBS. The cells ($3 \times 10^7$ cells/tube/3 mL in RPMI) are incubated with different amounts of test compounds for 2 hrs at 37° C. and then stimulated with goat F(ab')2 anti-human IgM (5 μg/mL) (Invitrogen) for 17 minutes in a 37° C. water bath. The stimulated cells are spun down at 4° C. with centrifugation and whole cell extracts are prepared using 300 μL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt which is (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, that is crystalline, having at least four XRPD peaks, in terms of 2-theta, selected from about 11.3°, about 16.4°, about 21.0°, about 23.0°, about 28.1°, about 31.2°, and about 32.8°.

2. The salt of claim 1 that is a 1:1 stoichiometric ratio of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one to hydrochloric acid.

3. The salt of claim 1 characterized by a DSC thermogram having an endothermic peak at about 207° C.

4. The salt of claim 1 having a DSC thermogram substantially as shown in FIG. 1.

5. The salt of claim 1 having a TGA thermogram substantially as shown in FIG. 2.

6. The salt of claim 1 having at least five XRPD peaks, in terms of 2-theta, selected from about 11.3°, about 16.4°, about 21.0°, about 23.0°, about 28.1°, about 31.2°, and about 32.8°.

7. The salt of claim 1 having an XRPD profile substantially as shown in FIG. 3.

8. A pharmaceutical composition comprising a salt of claim 1 and a pharmaceutically acceptable carrier.

* * * * *